(12) United States Patent
Carlisle et al.

(10) Patent No.: US 10,350,352 B2
(45) Date of Patent: Jul. 16, 2019

(54) PNEUMATICALLY COUPLED FLUID CONTROL SYSTEM AND PROCESS WITH AIR DETECTION AND ELIMINATION

(71) Applicant: LEVERAGED DEVELOPMENTS LLC, Stratham, NH (US)

(72) Inventors: Jeffrey A. Carlisle, Stratham, NH (US); Lawrence M. Kuba, Nashua, NH (US)

(73) Assignee: TURNPOINT MEDICAL DEVICES, INC., Lambertville, NJ (US)

( * ) Notice: Subject to any disclaimer, the term of this patent is extended or adjusted under 35 U.S.C. 154(b) by 645 days.

(21) Appl. No.: 14/285,314

(22) Filed: May 22, 2014

(65) Prior Publication Data

US 2014/0350511 A1 Nov. 27, 2014

Related U.S. Application Data

(60) Provisional application No. 61/826,863, filed on May 23, 2013.

(51) Int. Cl.
 *A61M 1/10* (2006.01)
 *A61M 5/36* (2006.01)
 (Continued)

(52) U.S. Cl.
 CPC ........ *A61M 5/16831* (2013.01); *A61M 1/106* (2013.01); *A61M 5/1452* (2013.01);
 (Continued)

(58) Field of Classification Search
 CPC .... A61M 39/24; A61M 5/365; A61M 5/1452; A61M 1/106; A61M 5/16859;
 (Continued)

(56) References Cited

U.S. PATENT DOCUMENTS 4,778,451 A 10/1988 Kamen
5,476,368 A 12/1995 Rabenau et al.
(Continued)

FOREIGN PATENT DOCUMENTS

CN 2875456 Y 3/2007
JP 63503116 A 11/1988
(Continued)

OTHER PUBLICATIONS

International Search Report and Written Opinion dated Apr. 6, 2015 received in PCT/US14/39207.
(Continued)

*Primary Examiner* — Lauren P Farrar
(74) *Attorney, Agent, or Firm* — McLane Middleton, Professional Association

(57) ABSTRACT

A fluid control system for delivery of a liquid includes a pneumatic drive that incorporates a linear actuator to effect known volume changes in a gas reservoir. The gas reservoir is in fluid communication with a gas-side reservoir that is separated from a fluid-side reservoir by a flexible membrane. Movement of the linear actuator effects positive or negative volume differences on the gas in the gas-side reservoir, resulting in a decrease or increase in pressure of the gas that is transmitted to the fluid-side reservoir to draw fluid, primarily liquid, in from a source or deliver liquid out to a sink. In another aspect, a mechanism is provided for the detection and elimination of air bubbles in the fluid path.

11 Claims, 24 Drawing Sheets

(51) Int. Cl.
  *A61M 5/38*    (2006.01)
  *A61M 39/24*   (2006.01)
  *A61M 5/142*   (2006.01)
  *A61M 5/145*   (2006.01)
  *A61M 5/155*   (2006.01)
  *A61M 5/168*   (2006.01)
  *A61M 5/172*   (2006.01)

(52) U.S. Cl.
  CPC ........ *A61M 5/14224* (2013.01); *A61M 5/155* (2013.01); *A61M 5/16822* (2013.01); *A61M 5/16854* (2013.01); *A61M 5/16859* (2013.01); *A61M 5/16881* (2013.01); *A61M 5/365* (2013.01); *A61M 39/24* (2013.01); *A61M 5/14593* (2013.01); *A61M 5/172* (2013.01); *A61M 5/385* (2013.01); *A61M 2005/14208* (2013.01); *A61M 2005/14513* (2013.01); *A61M 2039/242* (2013.01); *A61M 2205/123* (2013.01); *A61M 2205/128* (2013.01); *A61M 2205/3306* (2013.01); *A61M 2205/3331* (2013.01); *A61M 2205/3337* (2013.01); *A61M 2205/3379* (2013.01)

(58) Field of Classification Search
  CPC .......... A61M 5/14224; A61M 5/16822; A61M 5/155; A61M 5/16881; A61M 5/16854; A61M 2205/3379; A61M 2205/3331; A61M 2205/128; A61M 2205/123; A61M 5/172; A61M 5/16831; A61M 5/14593; A61M 5/385; A61M 2005/14208; A61M 2005/14513; A61M 2039/242; A61M 2205/3306; A61M 2205/3337
  See application file for complete search history.

(56) References Cited

U.S. PATENT DOCUMENTS

| | | | |
|---|---|---|---|
| 5,516,429 A | | 5/1996 | Snodgrass et al. |
| 5,669,764 A | | 9/1997 | Behringer et al. |
| 5,779,674 A | | 7/1998 | Ford |
| 5,785,688 A | | 7/1998 | Joshi et al. |
| 6,109,881 A | | 8/2000 | Snodgrass et al. |
| 6,302,653 B1 | * | 10/2001 | Bryant .................... F04B 51/00 417/383 |
| 6,419,841 B1 | | 7/2002 | Snodgrass et al. |
| 6,464,474 B2 | | 10/2002 | Schluecker |
| 6,494,694 B2 | | 12/2002 | Lawless et al. |
| 6,604,908 B1 | | 8/2003 | Bryant et al. |
| 6,749,403 B2 | | 6/2004 | Bryant et al. |
| 6,814,547 B2 | | 11/2004 | Childers et al. |
| 6,948,914 B2 | | 9/2005 | Kragelund et al. |
| 7,503,903 B2 | | 3/2009 | Carlisle et al. |
| 7,654,982 B2 | | 2/2010 | Carlisle et al. |
| 7,753,884 B2 | | 7/2010 | Gallnbock |
| 7,847,276 B2 | | 12/2010 | Carlisle et al. |
| 7,895,882 B2 | | 3/2011 | Carlisle et al. |
| 7,951,114 B2 | | 5/2011 | Rush et al. |
| 7,959,606 B2 | | 6/2011 | Rush et al. |
| 7,959,715 B2 | | 6/2011 | Kavazov et al. |
| 8,034,027 B2 | | 10/2011 | Comment et al. |
| 8,066,671 B2 | | 11/2011 | Busby et al. |
| 8,067,760 B2 | | 11/2011 | Carlisle et al. |
| 8,079,983 B2 | | 12/2011 | Rush et al. |
| 8,079,984 B2 | | 12/2011 | Rush et al. |
| 8,083,718 B2 | | 12/2011 | Rush et al. |
| 8,147,447 B2 | | 4/2012 | Sundar et al. |
| 8,172,800 B2 | | 5/2012 | Rush et al. |
| 8,215,930 B2 | | 7/2012 | Burden et al. |
| 8,382,711 B2 | | 2/2013 | Dudar et al. |
| 8,382,771 B2 | | 2/2013 | Gellman et al. |
| 8,409,441 B2 | | 4/2013 | Wilt |
| 8,876,756 B2 | | 11/2014 | Carlisle et al. |
| 9,339,602 B2 | | 5/2016 | Carlisle et al. |
| 2001/0028937 A1 | | 2/2001 | Powers et al. |
| 2002/0004015 A1 | | 1/2002 | Carlisle et al. |
| 2005/0069425 A1 | | 3/2005 | Gray et al. |
| 2005/0184087 A1 | | 8/2005 | Zagars et al. |
| 2006/0149211 A1 | | 7/2006 | Simpson et al. |
| 2007/0253463 A1 | | 11/2007 | Perry et al. |
| 2008/0097315 A1 | * | 4/2008 | Miner .................. A61M 5/1411 604/122 |
| 2008/0175719 A1 | * | 7/2008 | Tracey .................. A61M 1/369 417/38 |
| 2009/0035152 A1 | | 2/2009 | Butterfield |
| 2009/0131863 A1 | | 5/2009 | Carlisle et al. |
| 2010/0049133 A1 | | 2/2010 | Rush et al. |
| 2010/0057007 A1 | | 3/2010 | Rush et al. |
| 2010/0063765 A1 | | 3/2010 | Carlisle et al. |
| 2010/0100041 A1 | | 4/2010 | Rush et al. |
| 2010/0100042 A1 | | 4/2010 | Rush et al. |
| 2011/0028937 A1 | | 3/2011 | Powers et al. |
| 2011/0168270 A1 | | 7/2011 | Carlisle et al. |
| 2011/0202032 A1 | | 8/2011 | Shih et al. |
| 2011/0251557 A1 | | 10/2011 | Powers |
| 2011/0270182 A1 | | 11/2011 | Breznock et al. |
| 2012/0041413 A1 | | 2/2012 | Carlisle et al. |
| 2012/0172800 A1 | * | 7/2012 | Dudar ..................... A61M 5/36 604/123 |
| 2012/0207627 A1 | | 8/2012 | Demers et al. |
| 2012/0302945 A1 | | 11/2012 | Hedmann et al. |

FOREIGN PATENT DOCUMENTS

| | | |
|---|---|---|
| JP | 2000509620 A | 8/2000 |
| JP | 2012196342 A | 10/2012 |

OTHER PUBLICATIONS

International Search Report and Written Opinion dated Dec. 9, 2014 received in PCT/US14/39211.
European search report received in EP148018514.2 dated Nov. 18, 2016.
European search report received in EP148018805.4 dated Oct. 11, 2016.
Search Report dated Aug. 23, 2017, received in Chinese Patent Application No. 201480036040X.

* cited by examiner

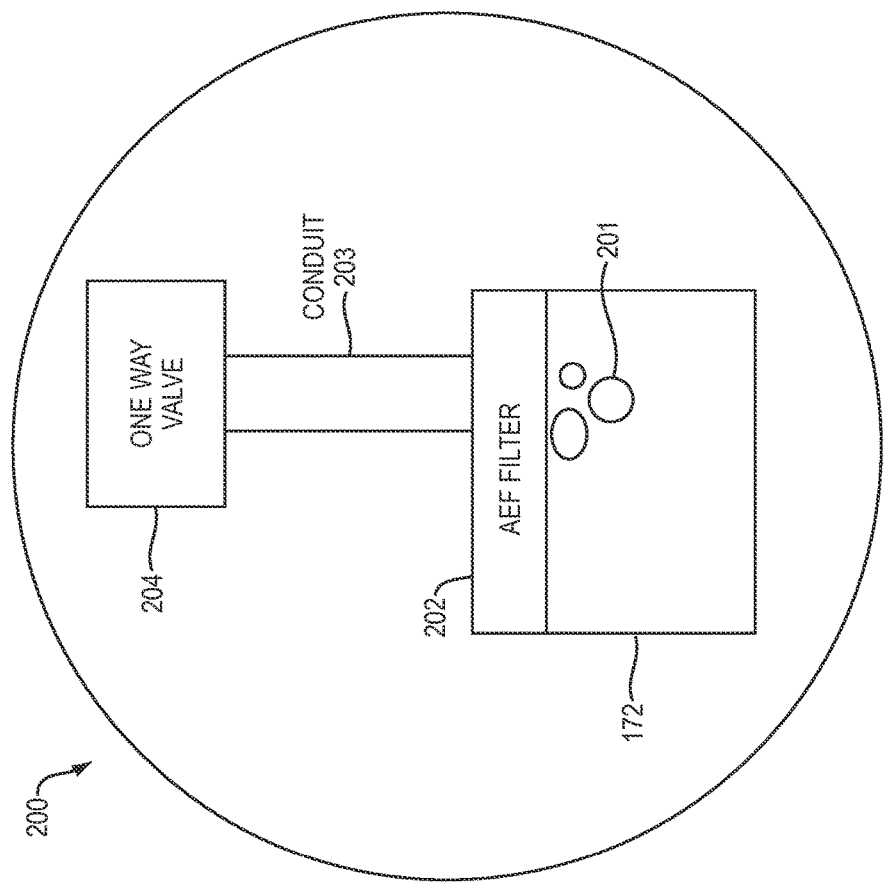
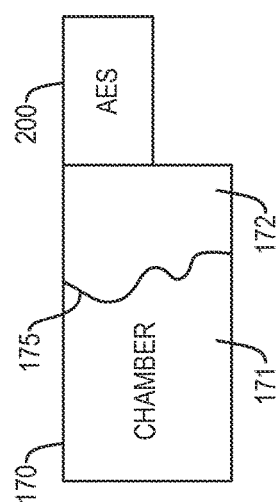
FIG. 4B
FIG. 4A

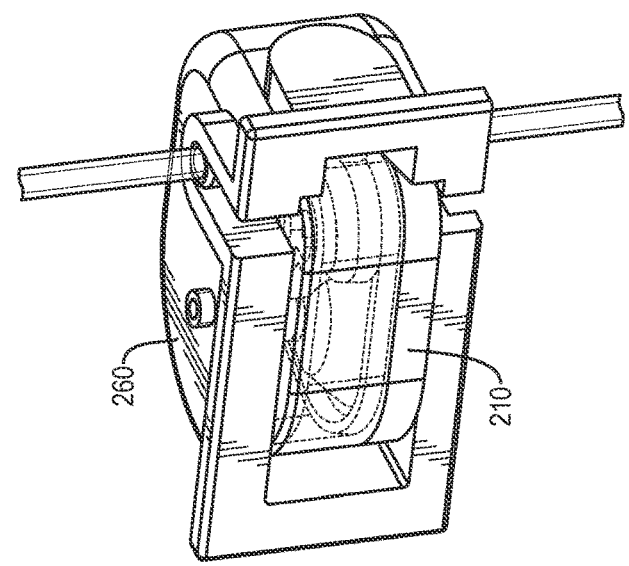
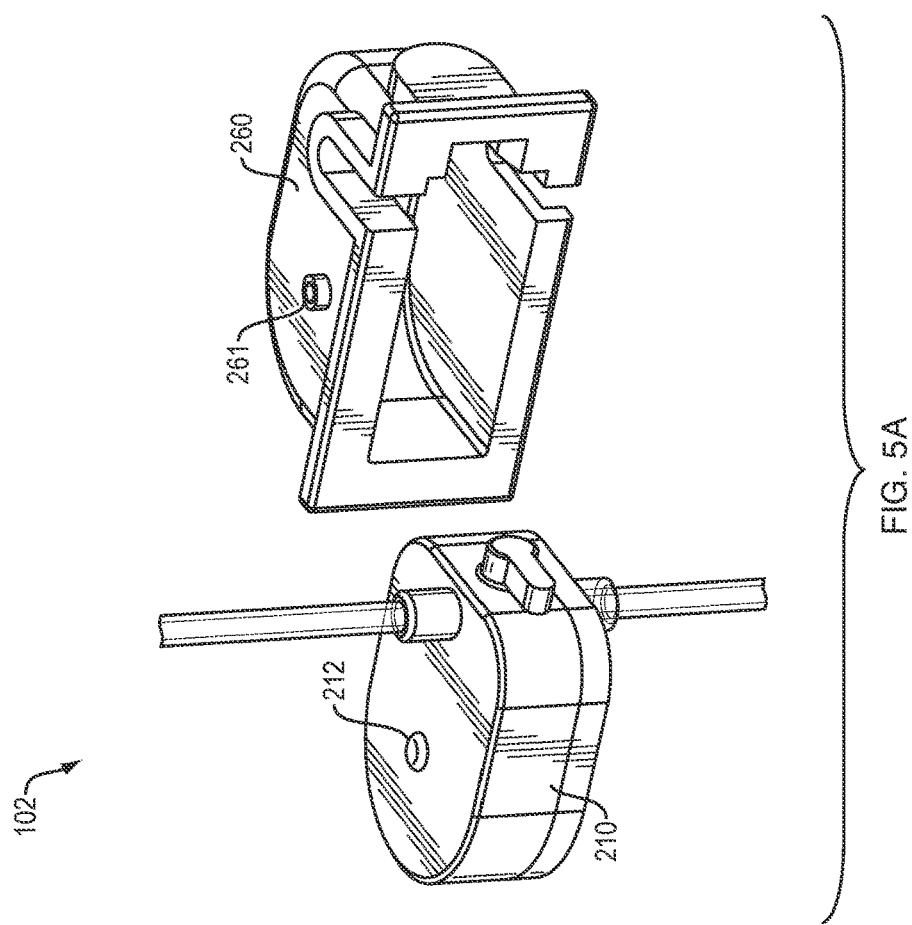

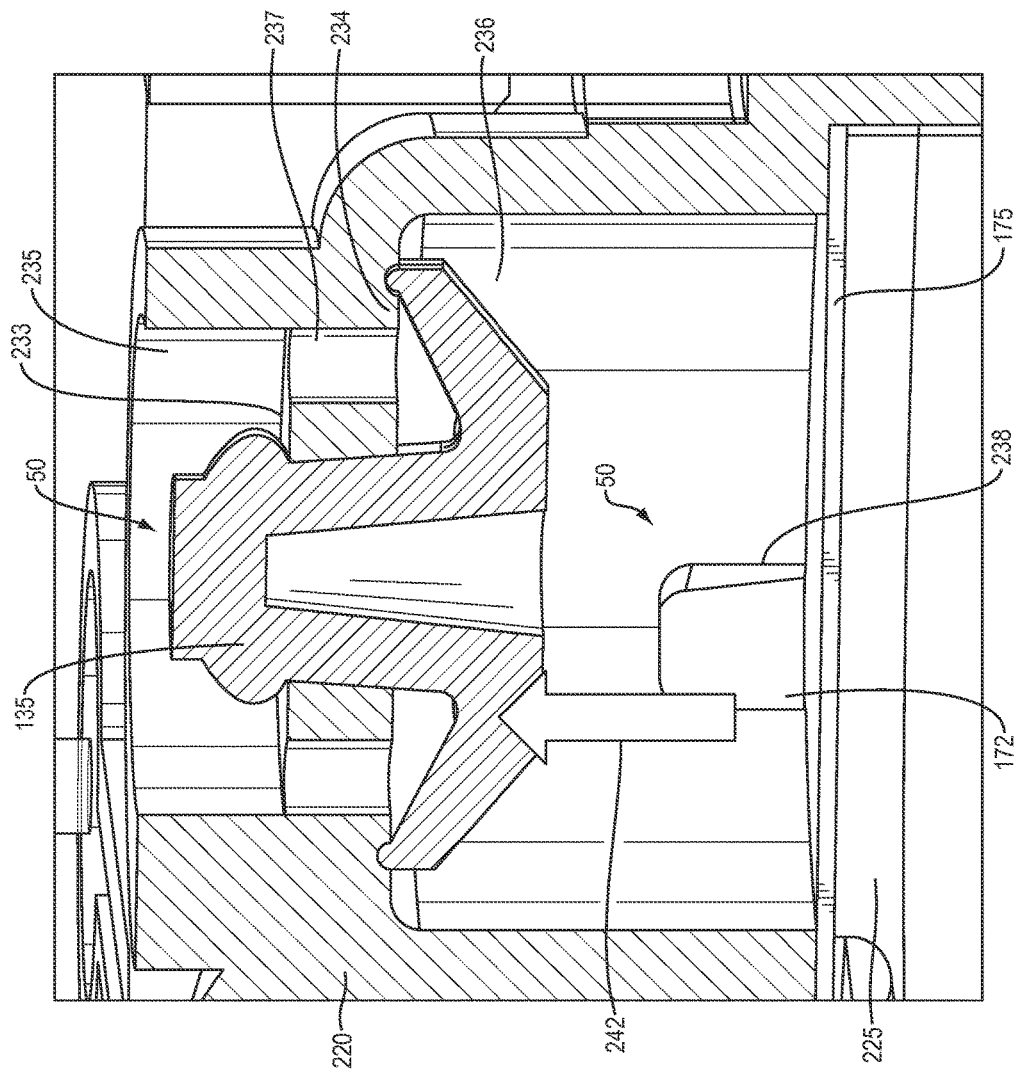

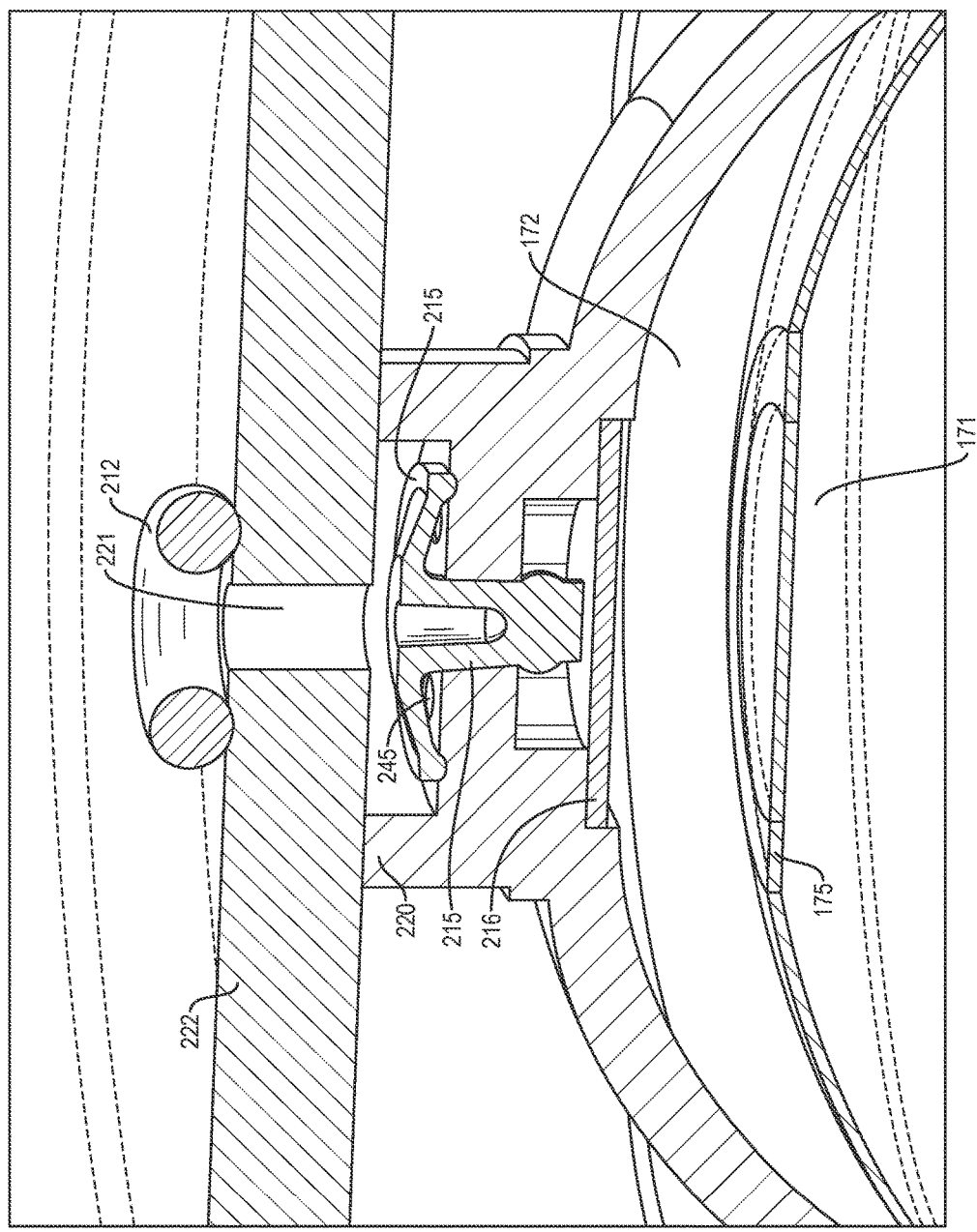

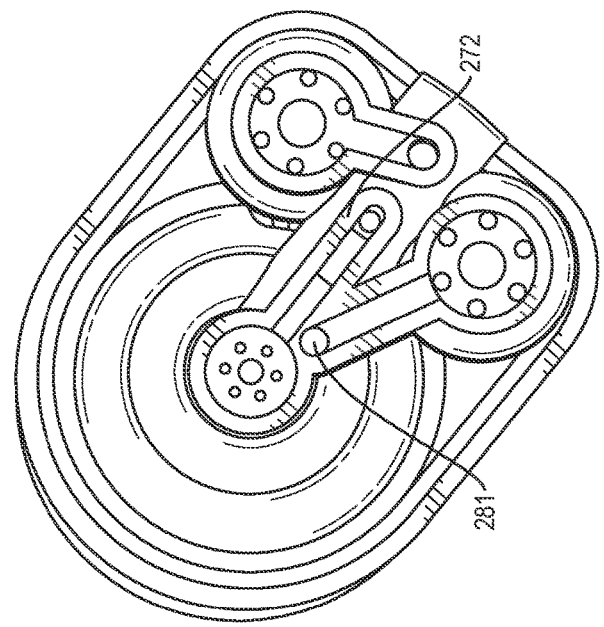
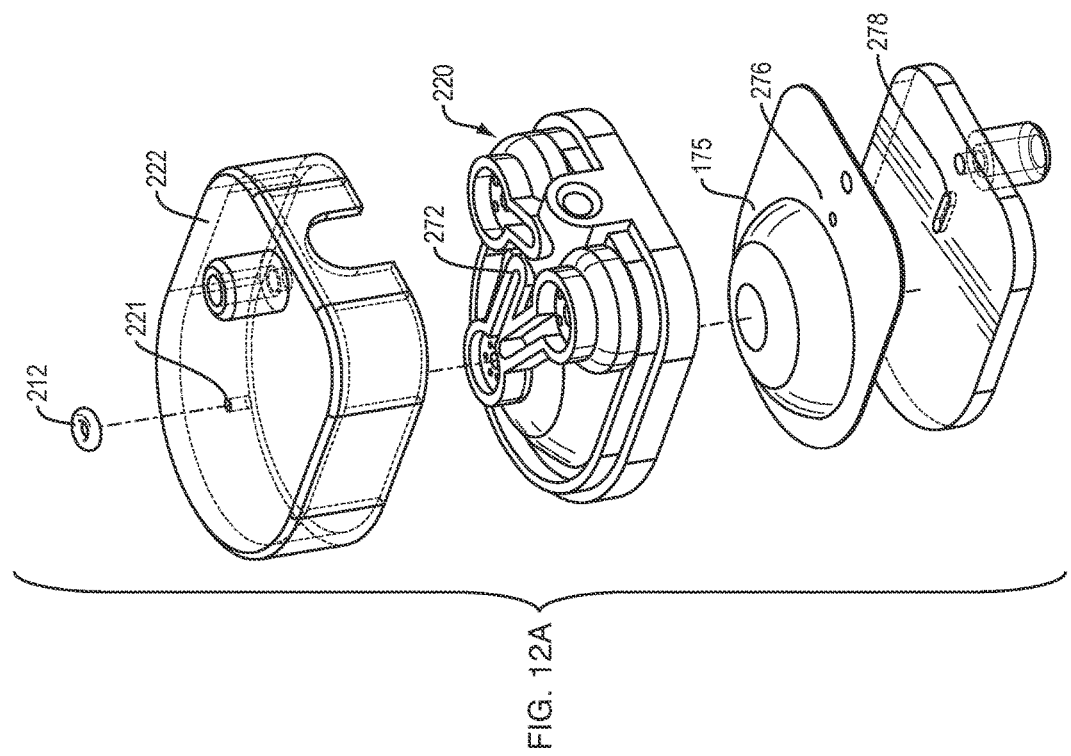

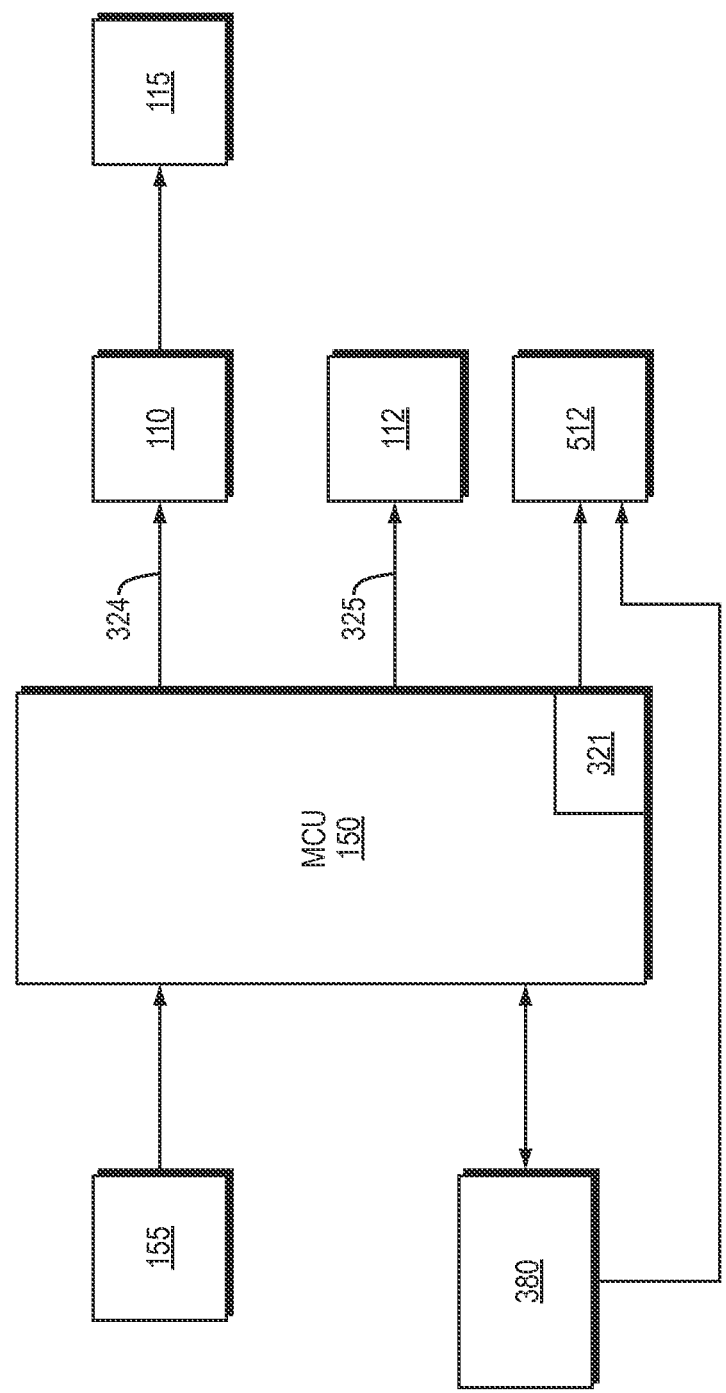

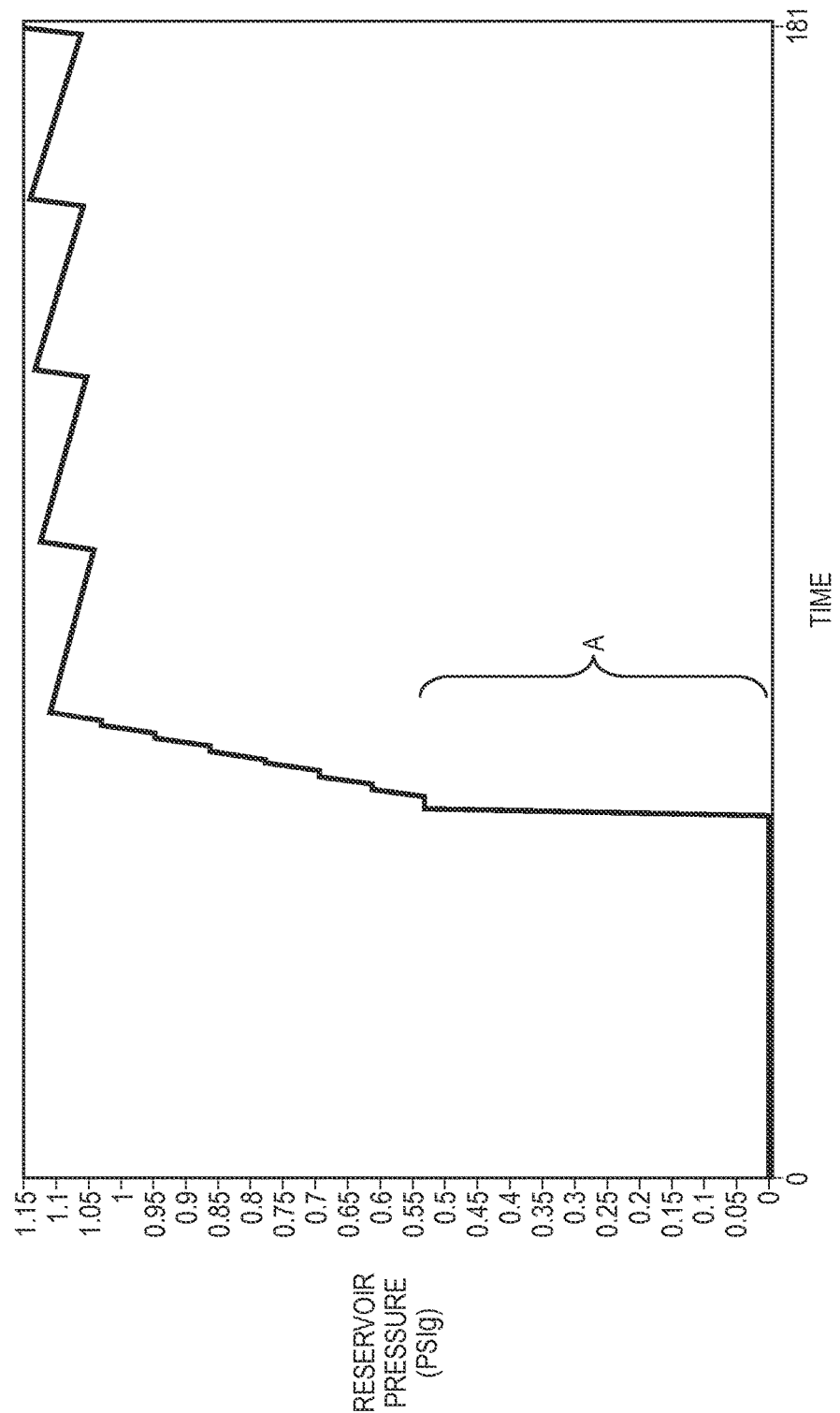

PNEUMATICALLY COUPLED FLUID CONTROL SYSTEM AND PROCESS WITH AIR DETECTION AND ELIMINATION

CROSS-REFERENCE TO RELATED APPLICATIONS

This application claims the benefit under 35 U.S.C. § 119(e) of U.S. Provisional Patent Application No. 61/826,863, filed May 23, 2013, the disclosure of which is incorporated by reference herein.

BACKGROUND

Fluid flow control is an essential part of medical devices such as intravenous infusion pumps and enteral feeding systems. These fluid flow control systems must meet a complex and conflicting set of requirements, such as broad flow rate range, wide ranging fluid viscosity, inevitable presence of harmful amounts of gas, changing source pressure, changing patient pressure, variable patient line resistance, and a wide range of tubing configurations.

Reliability and ability to detect fault conditions are critical features of such flow control devices. Low acquisition and maintenance costs are important characteristics also.

The usability of the system is vitally important, as it impacts the workflow of caregivers, which has a strong, but indirect, impact on the quality of patient care. This usability includes ease of loading the sterile tubing set, the need for attention from the caregiver during the fluid delivery period, and attending to unnecessary alarm conditions.

Conventional fluid control or pumping mechanisms suffer from an unfavorable tradeoff between sophistication and complexity. The added complexity of many modern systems has led to a lack of reliability, resulting in product performance failures, high levels of maintenance, product recalls by regulatory agencies, and documented high rates of patient harm.

One of the earlier types of fluid pump, as marketed by Harvard Apparatus Company and as replicated in the market hundreds of times thereafter, is a syringe pump. In a syringe pump, fluid is contained within a commonly found glass or plastic syringe, manufactured with a well-specified diameter and stroke length. These are the same syringes that are used to provide manual injections of sterile fluid. The piston of the syringe is securely held and, usually with a lead screw mechanism, the piston is advanced in carefully timed steps of a motor. Each step of the motor expresses a known amount of liquid out of the syringe and into a line going to the vasculature of the patient. The syringe pump offers a very simple mechanism and an extraordinarily simple control system, consisting of a timer circuit, set by the desired fluid flow rate. Force and position sensors are often added to provide feedback regarding occlusions, misloading, and end of infusion. The syringe pump design is inherently limited, however, by the relatively small size of the syringe, in the amount of fluid infused and in the maximum fluid flow rate, so this design does not satisfy the needs of many clinical applications. Ironically, at the very small volumes and flow rates, the syringe pump suffers from a discontinuity of fluid flow, based on the high static friction of the syringe. Very small movements of the drive motor do not necessarily translate into movement of the piston and delivery of fluid; it may take multiple motor steps and multiple time intervals before the piston actually delivers fluid to the patient. Long delay periods between delivery are not desirable clinically. A further deficiency in the syringe pump is the improper impedance match with the patient's vasculature; the syringe pump motor drive is equipped with a motor that is capable of reliably meeting the maximum torque foreseen by the system. This powerful motor is also geared down such that very low displacements can be achieved, giving the pump the ability to deliver at low flow rates. The combination of the powerful motor and the gearing, however, allows the syringe drive to generate fluid pressures that are far in excess of those needed to safely infuse a fluid into the vasculature of a patient. The consequence of this potentially high pressure output is that harmful levels of fluid pressure can be applied to the patient, with deleterious effects, especially in the event of an extravasation of the infusion catheter or the creation of a bolus upon release of a temporary occlusion.

Variations of the syringe pump are to be found in the form of a reciprocating piston that can draw from a fluid bag or vented bottle. Such devices, as found with the Abbott/Hospira Plum™ infusion device, overcome the volume limitation of a syringe pump. Added complexity for valving serves to increase cost and reduce reliability. A large volume pump, because of its multiple fluid connections and air spaces, creates an environment, not found with syringe pumps, for the introduction of harmful air bubbles, which must be detected and accommodated. These reciprocating piston pumps still retain the disadvantage of impedance mismatch described above for syringe pumps.

The most common form of infusion pump is the peristaltic pump, whereupon fingers or rollers occlude a section of flexible tubing in peristaltic fashion, expressing fluid out the tube toward the patient. This mechanism provides the simplest configuration to carry the sterile fluid in the form a simple flexible tube. The peristaltic pump suffers the same impedance mismatch fate as the syringe pump, because the forces required to faithfully occlude a portion of the flexible tube are great, allowing the pump to generate harmfully high infusion pressures. This potentially high pressure can be mitigated through the use of force sensors on the tubing, adding complexity and cost. The problem with air ingress to the patient is the same as with the reciprocating piston pump described above. The peristaltic pump introduced a new problem related to fluid flow accuracy, since the amount of fluid expressed to the patient is entirely dependent on the interior diameter of the fluid tubing in its uncompressed state. In fact the surface area error is a square law function of the error in the diameter, so a 10% error in the diameter would yield an unacceptable 21% ($1.1^2$) error in the volume expressed to the patient. Unfortunately, there are two very common events that can reduce the effective diameter of the tubing: one is the fatigue of the tubing as it is repeatedly worked by the peristaltic mechanism and the other is the failure of the tubing to refill completely due to low flow from the fluid source.

There is another class of pumps providing single flow rates using a constant force spring, membrane, or gas reaction pushing fluid against a fixed, calibrated resistance. These devices do not provide the programmable variation of flow rate needed for most clinical applications.

One variation of the reciprocal piston pump was designed and marketed by FluidSense Corporation of Newburyport, Mass. It used a flexible membrane connected to a spring-loaded piston on one side and sterile fluid on the other. A low cracking pressure passive inlet valve and an actively operated momentary outlet valve provided for a pumping action if the spring loaded piston were "cocked" back to load the spring, providing a positive fluid force. A highly sensitive linear encoder was used to watch the position of the spring-loaded piston, providing information on the fluid pressure and volume. This design allowed for a simplified and more sensitive pump mechanism, but the flow was intermittent with the action of each pulse of the outlet valve and the driving pressure varied from 3 to 7 PSIg, higher than necessary for most clinical applications. It also suffered from the introduction of air bubbles, as with all large volume pumping systems.

Programmable infusion devices, as opposed to single rate delivery systems, all suffer from two effects of electromechanical complexity. First, there are usually tight mechanical tolerances which can be disturbed by shock, vibration, temperature shifts, and aging. Infusion pumps are often out of their performance specifications, sometimes intermittently, making troubleshooting very expensive and difficult. Secondly, these complex mechanisms are often difficult to disinfect. Customers have only recently become sensitized to the extremely high importance of disinfecting infusion pumps and other medical devices. Cross contamination of patients is one of the top healthcare issues in the acute care environment.

Another particular problem that patients and caregivers face with great regularly is the presence of air bubbles in the fluid path. Conventional infusion pumps observe a segment of tubing via an ultrasonic or optical detector circuit. They reliably detect bubbles with high sensitivity. Unfortunately, the specificity of these sensors is low, so false alarms are commonplace. When these bubbles are detected, three bad things happen. First, the pump goes into an alarm condition and fluid flow to the patient is halted, which can often cause harm to the patient by withholding needed medication. Second, the alarm at the bedside causes significant distress to the patient and the patient's family. Third, the alarm disrupts the nurse's workflow, taking time away from other patients and directing the nurse's attention toward the infusion pump and away from the patient.

Air eliminating filters are commonly found in infusion therapy administration sets. These filters fail to solve the problems identified above, because these filters do not function properly when exposed to negative gauge pressures if they are positioned proximal to the infusion pump. If these filters are placed below the infusion pump, then there is no way for the pump to verify that these filters are in place, so the alarms must still stay active. These filters must also incorporate hydrophilic filters, which are not compatible with certain medical fluids, such as whole blood.

SUMMARY OF THE INVENTION

The present invention relates to a fluid control system implemented as a pneumatically coupled direct drive. The system is reliable, tolerant of changing conditions, and sensitive to conditions that prevent the accurate delivery of fluid. The system provides a simple actuating mechanism coupled with a low-pressure, closed loop control system, which overcomes the limitations of prior art systems described above.

The pneumatic drive of the fluid control system incorporates a linear actuator that interfaces with a gas reservoir to effect known volume changes in the gas reservoir. In one embodiment, the linear actuator comprises a drive motor coupled to a mechanism that provides linear motion to push or pull a reciprocating element, such as a bellows or a piston, by known linear increments. The reciprocating element translates bi-directionally in one dimension and has a fixed, known cross-sectional area, for example, in a plane orthogonal to the direction of translation. Thus, translation by a known distance results in a known volume change within the gas reservoir. The reciprocating element interfaces with a gas, typically air, in the gas reservoir such that translation of the reciprocating element increases or decreases the gas volume in the gas reservoir. The motor can be moved in either direction to increase or decrease the gas volume. A pressure sensor in the gas reservoir senses the gas pressure therein. A vent valve to ambient is also provided in the gas reservoir.

The gas reservoir is in fluid communication with a divided fluid chamber. The fluid chamber is separated by a flexible membrane into a gas-side reservoir and a fluid-side reservoir. The gas in the gas-side reservoir is in fluid communication with the gas in the gas reservoir of the linear actuator. The fluid-side reservoir is filled primarily with a liquid, such as medication or a feeding solution for delivery to the vasculature of a patient. Reciprocal motion of the reciprocating element, e.g., the piston or bellows, under control of the drive motor, imposes positive or negative volume differences on the gas in the gas-side reservoir, which results in a decrease or an increase in the pressure of the gas. This in turn causes a flexing of the membrane, which communicates the pressure difference to any fluid in the fluid-side reservoir. Passive inlet and outlet check valves are disposed along the fluid flow path through the fluid-side reservoir. The inlet and outlet check valves open in response to the pressure changes in the fluid to create a unidirectional pumping action to move the fluid in through the inlet check valve and subsequently out through the outlet check valve.

The system includes a controller that operates the pneumatic drive. The controller is operable to control delivery of liquid to the fluid sink by determining a volume of liquid to be delivered as the difference between a target volume of liquid to be delivered and a volume of liquid already delivered and operating the pneumatic drive in increments calculated to deliver the volume of liquid to be delivered. The controller is operable to calculate the volume of liquid to be delivered at successive time intervals and update the volume of liquid already delivered after each calculation of the volume of liquid already delivered.

The controller receives sensed pressure data from the pressure sensor at regular time intervals, including before and after a controlled movement of the pneumatic drive, and compares the pressure data to a known change in gas volume resulting from said controlled movement. The controller calculates a volume of gas based on the pressure data and the known change in gas volume based on an ideal gas law relationship between the sensed pressure data and the known gas volume.

The controller is also operable to determine pressure trends indicative of various conditions, such as an impedance or a resistance in the fluid flow path from the fluid source or to the fluid sink. The impedance or the resistance in the fluid source can be indicative of, for example, an occlusion in a line on the fluid flow path, an amount of liquid remaining in the fluid source, a viscous liquid at the fluid source, or the presence of a syringe. The impedance or the resistance in the fluid flow path to the fluid sink can be indicative of, for example, an occlusion in a line on the fluid flow path or a disconnected connection to the fluid sink.

In another aspect, the fluid control system incorporates an air detection and active air elimination mechanism that has improved detection specificity and is operable to eliminate an unlimited amount of air so as to avoid the negative aspects of air bubbles. The air elimination mechanism includes a hydrophobic filter material that prevents passage of liquid and a one way valve through which air can leave the system.

DESCRIPTION OF THE DRAWINGS

The invention will be more fully understood form the following detailed description taken in conjunction with the accompanying drawings in which:

FIG. 4a is a schematic diagram of a pumping chamber of FIG. 1 including an air elimination system;

FIG. 4b is an expanded schematic diagram of the air elimination system of FIG. 4a;

FIG. 5a is an isometric view of one embodiment of a fluid administration set illustrating a cassette and a housing;

FIG. 5b is an isometric view of FIG. 5a illustrating the cassette inserted within the housing;

FIG. 6 is an exploded view of the cassette of FIG. 5a;

FIG. 8 is a cross-sectional view of an inlet valve in the cassette;

FIG. 9 is a cross-sectional view of an air valve in the cassette;

FIG. 12a is an exploded view of the cassette illustrating a pneumatic pathway within the cassette;

FIG. 12b is a top view of the cassette body illustrate the pneumatic pathway;

FIG. 13 is a schematic block diagram of an embodiment of a failsafe circuit incorporating an additional vent valve;

FIG. 14 is a graph of a pressure response to a known decrease in gas volume;

DETAILED DESCRIPTION OF THE INVENTION

Figure 1:
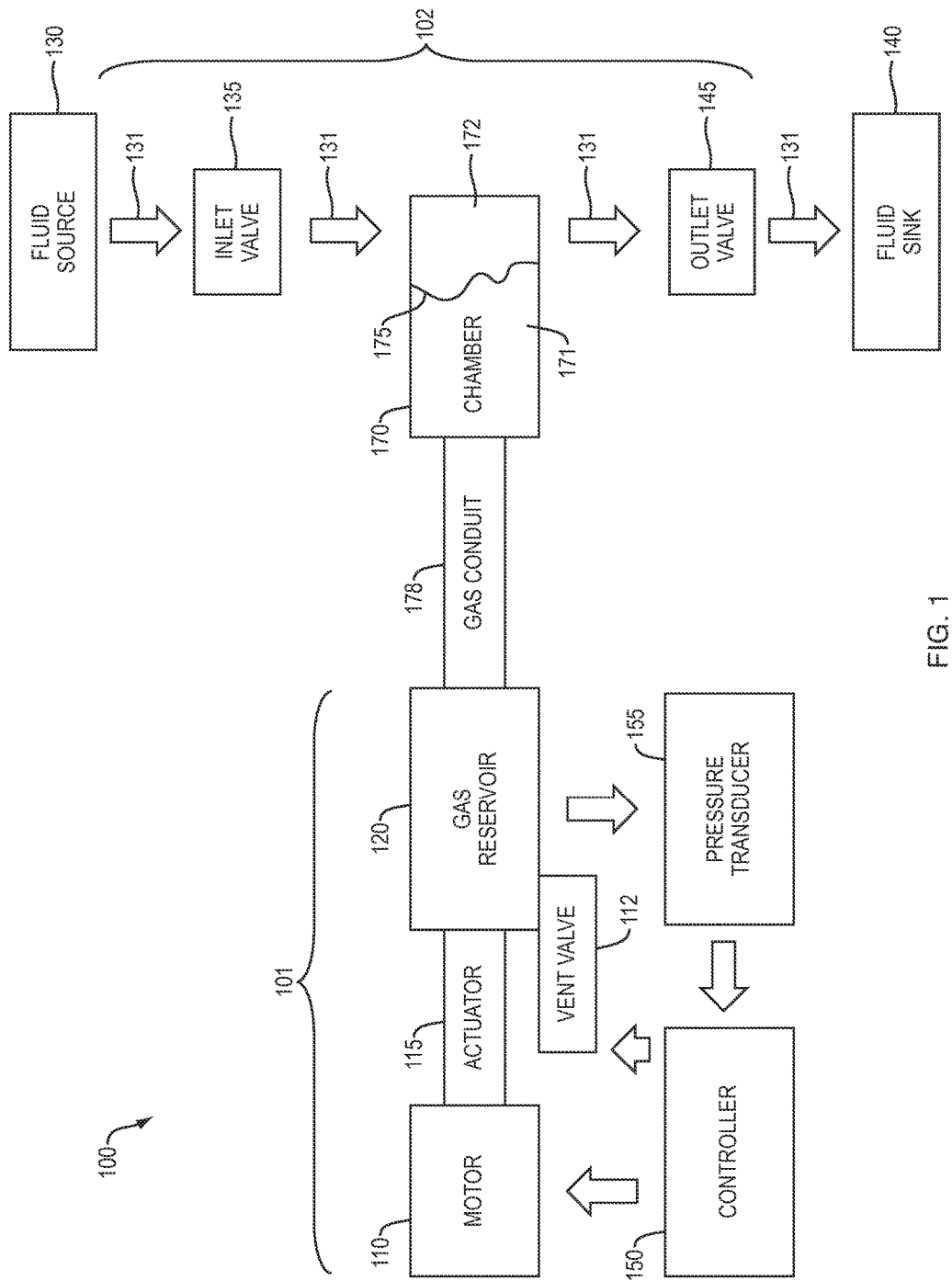
FIG. 1 is a schematic block diagram of one embodiment of a fluid control system.

FIG. 1 depicts a schematic block diagram for one embodiment of a fluid control system 100. The system incorporates a pneumatic drive 101 that interfaces with a fluid administration set 102 by which controlled amounts of fluid are withdrawn from a fluid source 130 and delivered to a fluid sink 140, such as the vasculature of a patient. The fluid control system can be embodied as a stand-alone pumping system or as a subassembly that is coupled to another pumping system that includes other components, such as a user interface, drug safety software, power supply, chassis, etc.

The fluid source 130 may be, e.g., a fluid contained within a flexible bag, a vented bottle, or a liquid filled syringe. The fluid flows on a flow path 131 through a pumping chamber 170, which is a rigid body or housing having a fixed volume. The chamber is divided by a flexible membrane 175 that is impermeable to gas or liquid into a gas-side chamber 171 and a fluid-side chamber 172. The flexible membrane 175 is sealingly fastened about its periphery within the chamber 170, but is otherwise free to move without restriction. Gas pressure within the gas-side chamber 171 imposes the same pressure within the fluid-side chamber 172. There is effectively no pressure differential across the flexible membrane 175. Pressure changes in the gas-side chamber are directly communicated to the fluid-side chamber via the flexible membrane and vice versa.

The fluid-side chamber 172 is disposed on the fluid flow path 131 and is in fluid communication with the fluid source 130 via an inlet valve 135. The fluid side chamber 172 is also in fluid communication with the fluid sink 140 via an outlet valve 145. The inlet valve and outlet valve each are passively operated one-way check valves and only open when the pressure differential between the upstream fluid and downstream fluid reaches a predetermined cracking pressure. The inlet valve 135 and outlet valve 145 each are normally closed to flow and require a relatively high differential pressure to open them in a forward direction. No practical amount of differential pressure can open them in the reverse direction. In one embodiment, suitable as a medical infusion pump, both valves 135, 145 are selected to have a relatively high cracking pressure, on the order of 1 PSId. The particular cracking pressure depends on the application, as would be appreciated by one of skill in the art.

The system also includes a pneumatic drive that is coupled to the gas-side chamber 171 to effect known incremental positive or negative volume changes that in turn cause positive or negative pressure changes in the gas-side chamber that are communicated to the fluid-side chamber 172. In one embodiment, the pneumatic drive includes a linear actuator, for example, a drive motor 110, such as a stepper motor or encoded DC motor or another electromechanical element that produces accurate incremental bi-directional movements. The drive motor is coupled to a cam or a lead screw mechanism or other mechanism that outputs linear motion. However, any linear actuator mechanism could be used, so long as its position is known and it has negligible hysteresis or backlash. The drive motor 110 is coupled to a reciprocating element 115 that reciprocates within a gas reservoir 120. The reciprocating element 115, e.g., a bellows or piston, translates bi-directionally in one dimension. Thus, translation by a known distance results in a known volume change. The reciprocating element interfaces with a gas, typically air, in the gas reservoir 120 such that translation of the reciprocating element increases or decreases the gas volume in the gas reservoir by a known amount. The reciprocating element 115 and gas reservoir 120 together form a syringe-like mechanism.

The gas reservoir 120 is in fluid communication with the gas-side chamber 171. A gas conduit 178 may be provided to fluidly connect the gas reservoir 120 with the gas-side chamber 171, depending on the configuration of the overall pumping system. A vent valve 112 is provided that can be opened to vent air in the gas reservoir to ambient. Momentarily opening the vent valve equilibrates the pressure in the reservoir 120 and connected space (gas conduit 178 and gas-side chamber 171) to atmospheric pressure. Any suitable vent valve can be used, such as an electromechanical solenoid valve. A pressure sensor 155, such as any suitable pressure transducer, is also provided to measure the pressure within the gas reservoir 120, which also provides a measure of the pressure in the gas-side chamber and the fluid-side chamber of the pumping chamber.

A system controller 150 is provided in operative communication with the motor 110 and the vent valve 112 and with the pressure sensor 155 to receive pressure data. The controller 150 includes a processor or microprocessor or the like and support electronics for communication, sensing, computation, and actuator control. The controller 150 includes non-volatile memory (e.g., ROM) for storage of data and instructions, volatile memory (e.g., RAM) for input and output, a clock, and an input/output (I/O) control unit. The controller 150 can be provided as a microcontroller unit on a single chip. The controller can also interface with another computer or controller that is part of an overall pumping system or pumping application, discussed further below.

The drive motor 110 is moved in known increments based on commands from the controller 150, which in turn moves the reciprocating element 115 a known length to achieve a known change in gas volume in gas reservoir 120. The volume change, in turn, results in a change in pressure in reservoir 120. The gas pressure seen at reservoir 120 and gas conduit 178 is equilibrated with the gas pressure within the gas-side chamber 171 and imposes the same pressure within the fluid-side chamber 172 by flexing of the flexible membrane 175, as there is no differential pressure across the membrane.

In one embodiment, the reciprocating element 115 of the linear actuator is formed as a bellows capable of controllable linear translation in one dimension. One end of the bellows is sealingly fixed to a rigid housing forming the gas reservoir 120 via, for example, a flange, and the other end of the bellows is coupled to the motor 110 for linear movement, via, for example, a flange or an end plate. Thus, the diameter or cross-sectional area of the bellows is effectively fixed and therefore known. The interior of the bellows is open to and forms part of the gas reservoir. Accordingly, when the bellows translates linearly, generally in a direction orthogonal to the plane of the end plate of known diameter, the volume change can be determined from the length of translation multiplied by the cross-sectional area of the bellows. The length of translation is known, because it is determined by the incremental motion of the drive motor, which is controlled by the controller 150.

Implementation of the reciprocating element as a bellows is advantageous, because the bellows is capable of linear translation without stiction or friction against a housing. The bellows can be designed and fabricated with a known stroke length and spring rate and operating pressure range on both sides of the bellows. Any suitable material, such as stainless steel or another metal alloy, for example, a titanium alloy, can be used in forming the corrugations of the bellows. Suitable bellows are commercially available from, for example, BellowsTech, LLC, of Florida.

In another embodiment, the reciprocating element of the linear actuator is formed as a piston. The piston is coupled to the motor for linear translation within a cylinder that is coupled to or a part of the gas reservoir 120. The diameter or cross-sectional area of the piston end face (or cylinder) is fixed and known. Thus, as with the bellows, when the piston translates linearly, the volume change can be determined from the length of translation multiplied by the known, fixed cross-sectional area of the piston end face. The length of translation is known, because it is determined by the incremental motion of the drive motor, which is controlled by the controller 150. The linear actuator can also refer to an array of pistons, connected to a single drive motor. Various linear or rotary configurations of pistons can be used, for example, to meet packaging requirements.

The controller 150 can adjust pressure in three ways. To create increasing gauge pressure within the gas reservoir 120 by the linear actuator 115, which is then communicated to the gas-side chamber 171 and then to the fluid-side chamber 172, the controller 150 can move motor 110 in one direction, for example, clockwise. To create decreasing gauge pressure within the gas reservoir 120 by the linear actuator 115, which is then communicated to the gas-side chamber 171 and then to the fluid-side chamber 172, controller 150 can move motor 110 in the opposite direction, counterclockwise. To produce zero gauge pressure within the gas reservoir 120, which is then communicated to the gas-side chamber 171 and then to the fluid side reservoir 172, the controller 150 can activate the vent valve 112.

By way of an overview, in operation to perform a FILL step, the vent valve 112 is closed and the linear actuator 115 is retracted, which increases the volume and decreases the pressure in the gas reservoir 120 and gas-side chamber 171. The pressure in the fluid-side chamber 172 is similarly decreased, which leads to a pressure differential across the inlet valve 135. When the pressure differential reaches the cracking pressure of the inlet valve, the valve opens and fluid, primarily liquid, from the fluid source flows through the inlet valve into the fluid-side chamber, in a FILL step. To perform a DELIVER step, the vent valve is closed and the linear actuator is advanced. The pressure in the gas-side chamber and the fluid-side chamber increases, which leads to a pressure differential across the outlet valve 145. When the pressure differential reaches the cracking pressure of the outlet valve, the valve opens and liquid from the fluid-side chamber flows through the outlet valve to the fluid sink, in an DELIVER step.

Figure 2:
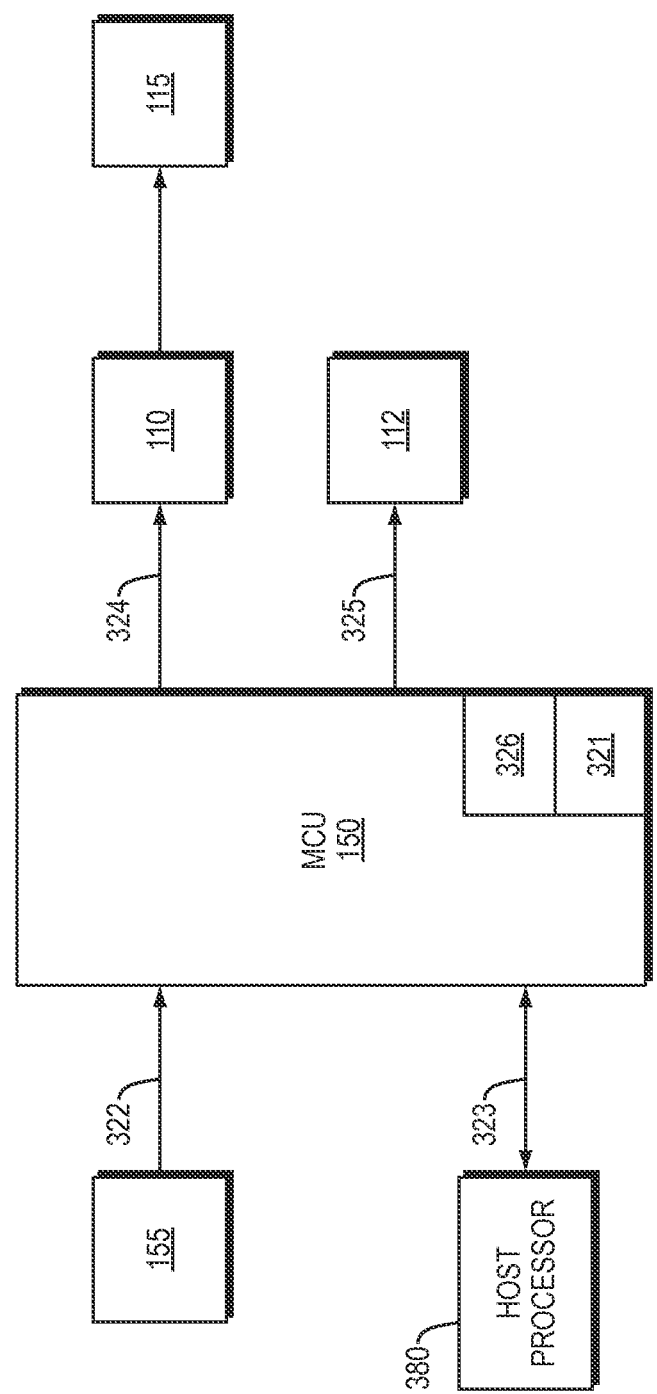
FIG. 2 is a schematic block diagram of a controller for use in the fluid control system of FIG. 1.

Referring now to FIG. 2, the controller 150 uses minimal inputs and outputs to achieve flow control for the system. A point along the travel of the linear actuator 115, a "home" or "park" position, is stored in storage 321. Maximum and minimum travel positions of the linear actuator during FILL and DELIVER steps are stored as well. Periodic measurements are made by the pressure sensor 155 and transmitted as a pressure signal 322 to the controller 150. Motor control signals 324 are transmitted to the motor drive 110 to move in either direction and over a wide range of speeds. The vent valve 112 is normally closed and can be opened programmatically via vent control signals 325. The controller also includes a clock 326 for timing.

Commands from another controller or a host processor 380 from, for example, an overall pumping system, can be exchanged digitally, for example, via serial communication link 323. Only a small number of supported commands and queries are needed. The communication link can use a common protocol such as Wi-Fi (IEEE 802 wireless standards), I2C, SPI, ZigBee, USB, TCP/IP, BTLE, or other protocols. The use of a high level, simple communications system allows for simplified software architecture and a more reliable verification process. The other controller 380 can reside on a mobile device, such as an iPhone, or a tablet device, such as an iPad, which contains a program or application (app) for receiving data from and transmitting instructions to the system controller 150.

Figure 3:
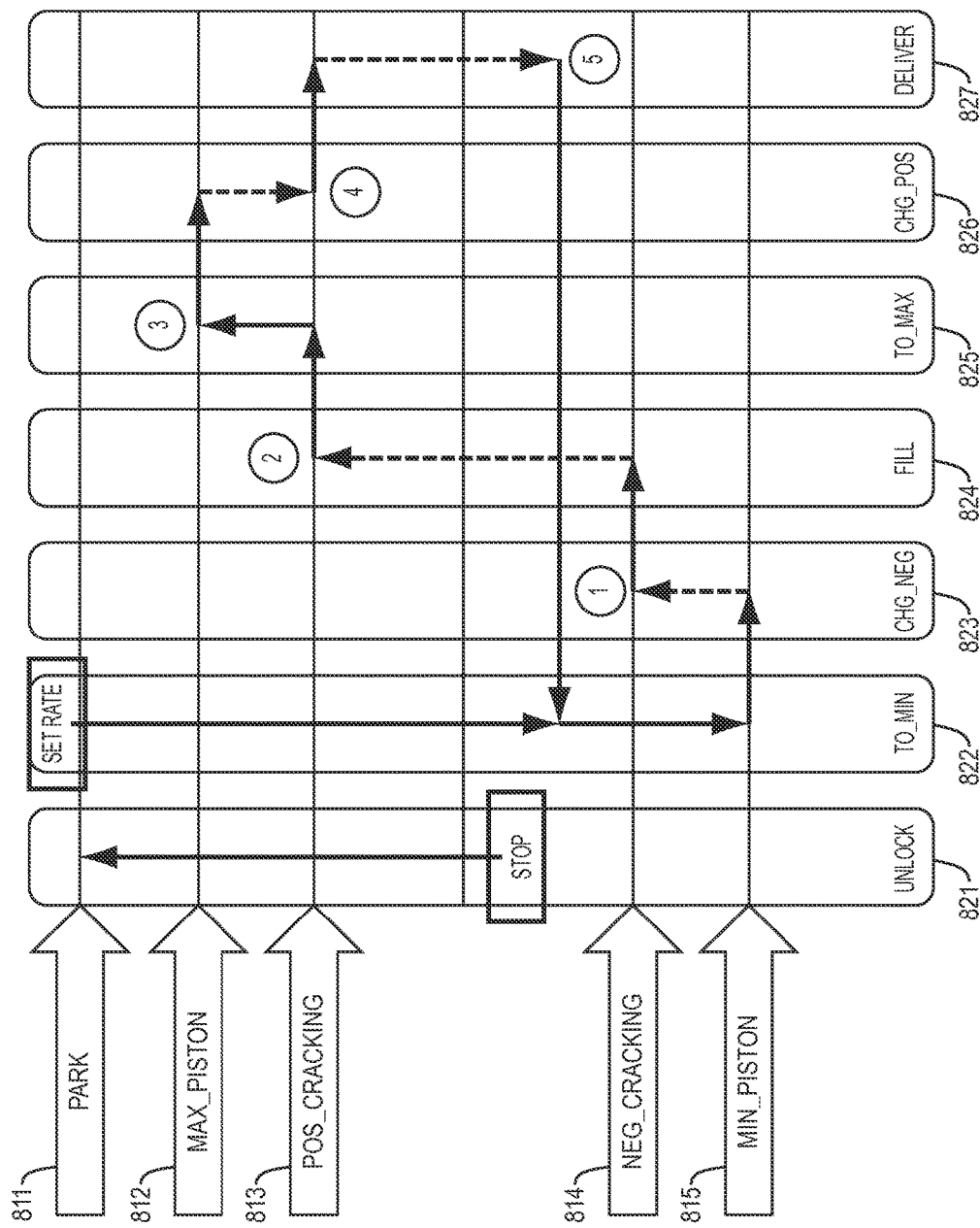
FIG. 3 is a schematic diagram illustrating positions of a linear actuator of the fluid control system at various states in a pumping cycle.
Figure 6:
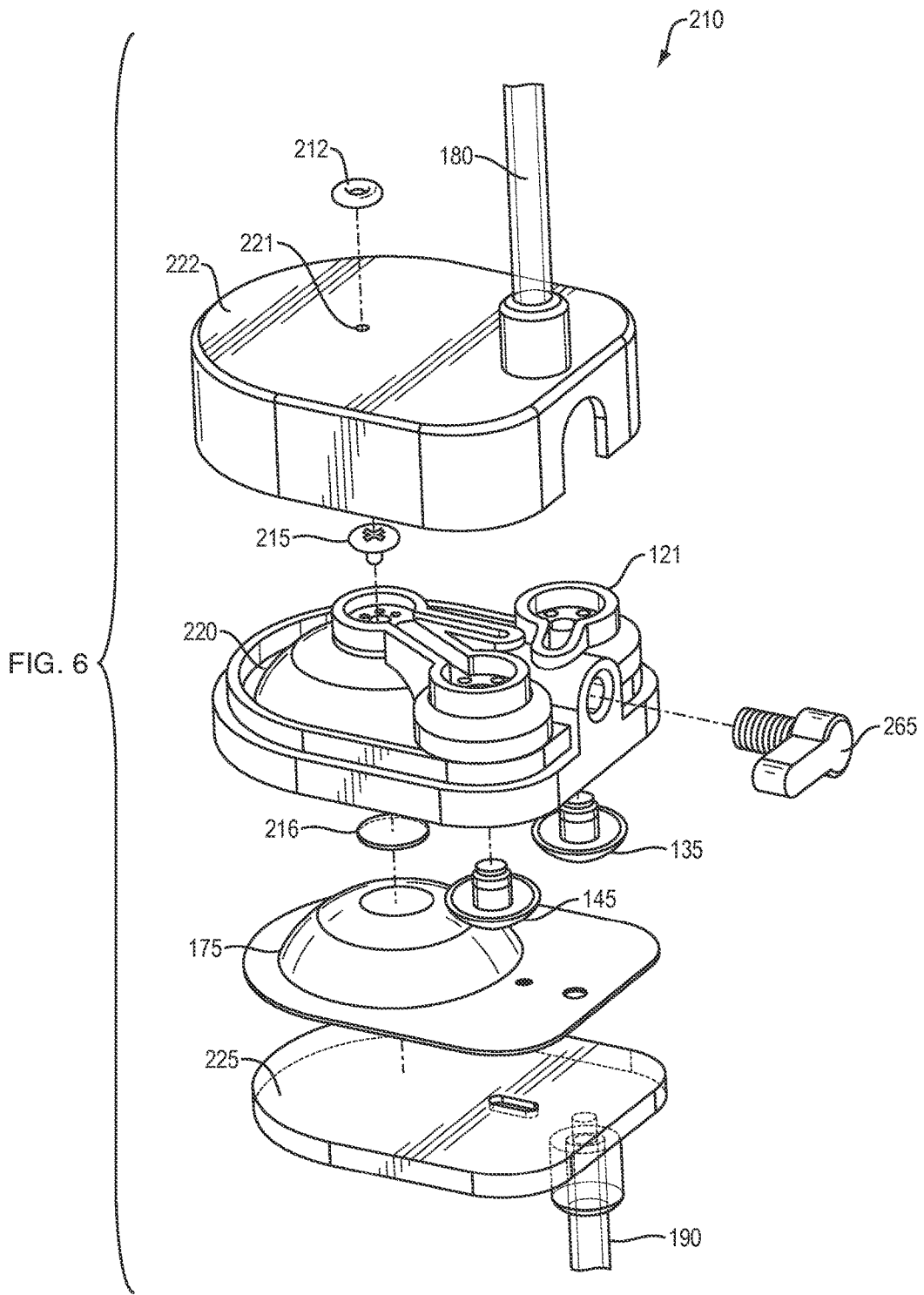

FIG. 3 shows various states and the association with positions of the linear actuator 115. The linear actuator 115 can be moved by the motor 110 under control of the controller 150 to any position. Certain positions along the entire stroke are described as follows. The positions PARK 811 (the "home" position), MAX (or MAX PISTON) 812 (the position at which the linear actuator is fully retracted during a pumping cycle), and MIN 815 (or MIN PISTON) (the position at which the linear actuator is least retracted (or fully advanced) during a pumping cycle) are fixed positions by design. The position POS CRACKING 813 (when the outlet valve opens) and position NEG CRACKING 814 (when the inlet valve opens) are variable, depending upon the conditions of the infusion. The controller 150 includes instructions that maintain the system in one of several states, which determine the movement of the linear actuator 115 and the interpretation of the pressure signal 322. When idle, the system is in the state UNLOCK 821 and the linear actuator is brought to the position PARK 811. Upon instruction to begin an infusion (which may be transmitted by the host processor 380), the controller 150 enters the state TO MIN 822 and the linear actuator 115 is brought to the position MIN 815 with the vent valve 112 open. Once the infusion begins, the controller 150 enters the state CHANGE NEG 823 and with the vent valve closed, the linear actuator 115 is gradually moved (retracted) until the inlet valve 135 opens at the position NEG CRACKING 814. The state FILL 824 begins, during which the fluid-side reservoir 172 fills with liquid from the source, and continues until the fluid-side reservoir 172 reaches its maximally filled position. In preparation to deliver fluid to the fluid sink 140, the controller 150 moves the linear actuator 115 to the position MAX 812 with the vent valve 112 open in the state TO MAX 825. The controller 150 enters the state CHANGE POS 826 and with the vent valve closed, the linear actuator 115 is gradually moved (advanced) until the outlet valve 145 opens at position POS CRACKING 813. Finally, the linear actuator 115 advances at a speed to deliver the proper amount of fluid in the state DELIVER 827. When the state DELIVER 827 is complete, the controller 150 reverts back to the state TO MIN 822, continuing the cycle until the set target is complete.

The reservoir 120 with connected dead space of the gas conduit 178 and the pumping chamber 175 has a finite volume. The linear actuator 115 has a finite length of travel and can reach the limits of its position in either direction. If the controller 150 seeks an increase in pressure when the linear actuator 115 is at position MIN 815, then it must move the linear actuator towards position MAX 812 while the vent valve 112 is open. The use of the vent valve allows movement of the linear actuator without the generation of any pressure changes. Once the position MAX 812 is reached, then the vent valve 112 is closed and the linear actuator is moved towards the position MIN 815, reducing the effective volume of the reservoir 120 and increasing the pressure of the gas-side chamber 171. Similarly, if the controller 150 seeks a decrease in pressure when the linear actuator 115 is at the position MAX 812, then it must move the linear actuator towards position MIN 815 while the vent valve 112 is open. Once the position MIN 815 is reached, then the vent valve 112 is closed and the linear actuator is moved towards the position MAX 812, increasing the effective volume of the reservoir 120 and decreasing the pressure of the gas-side chamber 171. With the vent valve closed, the displacement of the linear actuator 115 from the position MAX 812 to the position MIN 815 creates a change in volume and a subsequent change in pressure large enough that it exceeds the cracking pressure of the outlet valve. With the vent valve closed, the displacement of the linear actuator 115 from the position MAX 812 to the position MIN 815 creates a change in volume and a subsequent change in pressure large enough to exceed the cracking pressure of the outlet valve. Similarly, with the vent valve closed, the displacement of the linear actuator from the position MIN to the position MAX creates a change in volume and a subsequent change in pressure large enough to exceed the cracking pressure of the inlet valve.

FIG. 4a depicts a portion of FIG. 1 illustrating an air elimination system (AES) 200 that forms part of the fluid control system 100. FIG. 4b depicts a detailed view of the elements of the air elimination system 200. Air bubbles 201 are shown within the fluid-side chamber 172, which is in direct contact with a hydrophobic filter 202. The other side of the hydrophobic filter communicates via a conduit 203 with a one way valve 204, such as a check valve, leading to atmosphere.

In the course of filling and emptying the fluid side chamber 172, air bubbles 210 can enter fluid side chamber 172, for example, as a result of out-gassing, making new fluidic connections, emptying fluid source containers, and the like. The fluid delivery comprises repeated cycles of filling and emptying the fluid-side chamber 172 by imposing negative and positive pressures in gas side chamber 171, allowing the flexible membrane 175 to freely move without differential pressure being developed. At the completion of a filling phase, negative pressure has been applied to the gas-side chamber 171 and to the fluid-side chamber 172, drawing fluid in from the fluid source 130 until such time that flexible membrane 175 hits a mechanical limit imposed by the chamber 170. Following the activation of the vent valve 112, the controller 150 issues a command to the motor 110 to move the actuator 115 forward, reducing the volume of gas reservoir 120. The resultant pressure change is measured, as discussed further below.

The cracking pressure of the outlet valve 145 must be substantially higher than the cracking pressure of one way valve 204. In the circumstance where air bubbles 201 are present and in surface contact with the hydrophobic filter 202 and where pressure in the fluid-side chamber 172 is greater than in the conduit 203, air bubbles 201 freely travel across the hydrophobic filter 202 until such time as there is no differential pressure across the hydrophobic filter 202. When gauge pressures in the conduit 203 are higher than the cracking pressure of the one way valve 204, air travels through the open one way valve into atmosphere. When the one way valve closes, the residual pressure in the conduit equals the cracking pressure of one way valve. Liquid is prevented from leaving or entering the system by virtue of the physical properties of the hydrophobic filter 202. Air from the atmosphere is prevented from entering the system due to the mechanical property of the one way valve 204.

In the filling phase of the system in which pressures in the fluid-side chamber 172 are negative, a small amount of air trapped and pressurized in the conduit 203 may re-enter the fluid-side chamber 172, serving to push or clear away a liquid barrier from the surface of the hydrophobic filter 202. This small amount of air is an insignificant volume relative to the fluid-side chamber 172, but does represent a regurgitation of volume that insignificantly reduces the efficiency of the pumping system. The clearing of the filter is, however, useful especially for long term infusions of colloidal suspensions, lipids, and other fluids with strong surface tension properties.

The air filter 202 and one way valve 204 can be located in any suitable location in the fluid-side chamber 172. In one embodiment, they are located in a rigid wall of the housing and vent gas to ambient. In another embodiment, they are located within the membrane 175 and vent gas into the gas-side chamber 171, discussed further below.

In one embodiment, the fluid control system is implemented as two subsystems. One subsystem encompasses the fluid administration set 102, incorporating the pumping chamber 170, including the gas-side chamber 171 and the fluid-side chamber 172, the membrane 175, and the inlet and outlet valves 135, 145. The fluid administration set can be disposable and can be maintained in a sterile condition. Tubing can be included as a part of the subsystem if desired, either attached to or attachable to the inlet and outlet valves.

The other subsystem encompasses the pneumatic drive 101, which can be readily connected to the fluid administration set 102 via the conduit 178 from the gas reservoir 120 to the gas-side chamber. The conduit 178 can be of any length, for example, up to 40 feet or more. With a conduit of greater length, the fluid administration subsystem can be removed from the vicinity of the pneumatic drive subsystem, which can be advantageous is some situations. For example, some patients are in imminent need of both an infusion of fluids and an MRI (magnetic resonance imaging) to, for example, detect internal bleeding. However, the electronics of most infusion pumps prevents these pumps from operating in the vicinity of the MRI equipment. Thus, these patients must either delay the MRI until a necessary infusion is complete, or delay the infusion until the MRI is complete. The fluid administration subsystem 102 of the present fluid control system, however, contains no electronics and can be used in the vicinity of MRI equipment. Thus, by employing a conduit of a suitably long length, the fluid administration subsystem 102 can be displaced a distance from the pneumatic drive subsystem 101 and can be taken into the vicinity of the MRI equipment, allowing the infusion to the patient to continue while the patient receives the MRI.

In one embodiment, referring to FIGS. 5a-12b, the fluid administration subsystem 102 is implemented as a removable, and if desired, disposable, cassette that is supported by a housing that, in turn, interfaces with the pneumatic drive 101. The cassette 210 creates a sterile pathway from the fluid source 130 to the fluid sink 140, i.e., the vasculature of a patient. A housing 260 interfaces with and retains the cassette 210 in place so that pressure can be conveyed to the membrane 175 from the pneumatic drive 101. The housing 260 creates an airtight interference fit with a cassette top 222, connecting an air sealing ring 212 with positive and negative air pressure connected to a pneumatic connection 261. Gas pressure generated in the linear actuator 115 is connected to the pneumatic connection 261 in the pump housing 260. When coupled with the cassette inserted into the pump housing, as shown in FIG. 5b, an airtight seal is created between the pneumatic connection 261 and the air sealing ring 212. The flat surface of the cassette top that interfaces with the housing 260, along with the pneumatic connection 261 that communicated from the linear actuator to the gas-side chamber 171, provide surfaces that can be readily kept clean and disinfected.

Referring to FIG. 4, the cassette 210 includes a rigid molded cassette body 220 that forms a sandwich configuration with a rigid plate cassette bottom 225 and with the flexible membrane 175. The membrane 175 is a highly flexible, impermeable feature of the cassette 210, separating the interior of the body into the fluid-side reservoir 172 and the gas-side reservoir 171, as discussed above. A gas filter 216 is secured into the cassette body 220. The inlet valve 135 and the outlet valve 145 are assembled into cassette body 220, oriented in such a way that fluid flow can only proceed from an inlet tube 180 towards an outlet tube 190. The inlet valve 135 is a one-way valve in the fluid path allowing flow from the source 130 to pumping chamber 170 defined by the cassette body 220 and the cassette bottom 225, after its cracking pressure is reached.

The membrane 175 and the cassette bottom 225 are bonded to the cassette body 220 to create a leak-free and sterile fluid pathway. An air check valve 215 is assembled into the cassette body 220, and the cassette top 222 is bonded to the cassette body 220. A Bypass screw 265 provides manual opening of the flow between the inlet tube 180 and the outlet tube 175 and provides for manual enablement of fluid flow when the cassette 210 is removed from the system. The air sealing ring 212 is attached to the cassette top 222 above the cassette sealing surface 221.

Figure 7B:
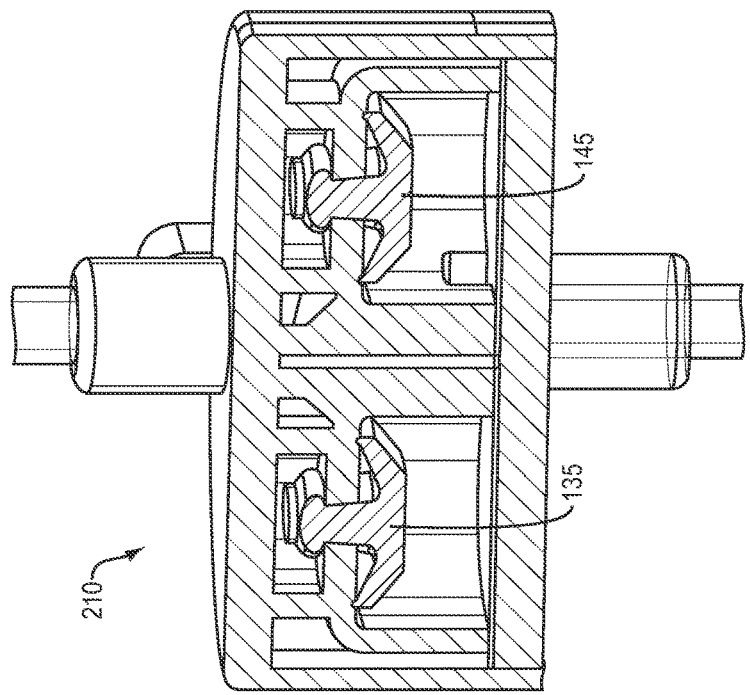
FIG. 7b is a further cross-sectional view of the cassette.
Figure 7A:
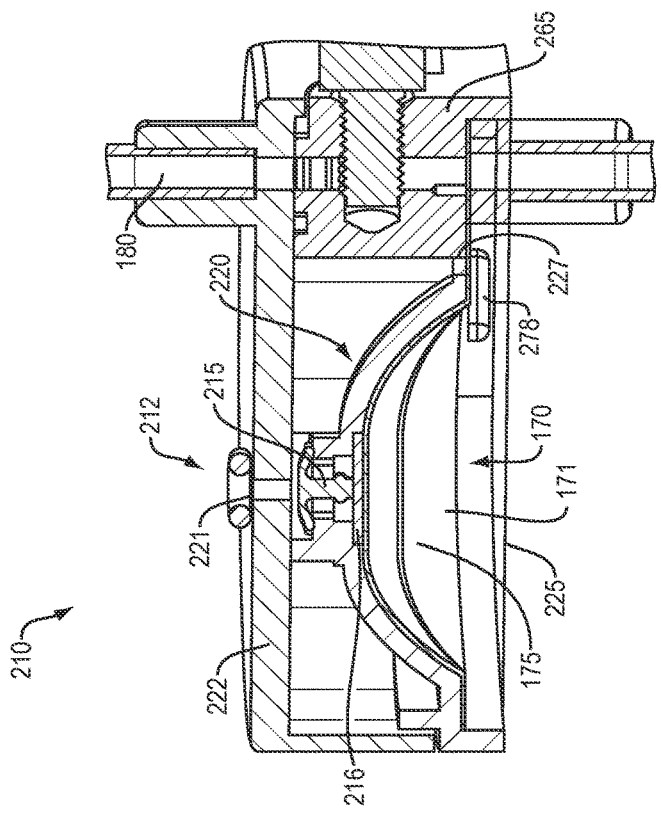
FIG. 7a is a cross-sectional view of the cassette.

FIG. 7a shows a cross-sectional view of the cassette 210. Gas pressure communicates through the gas sealing ring 212 and the cassette sealing surface 221. The pressure is normally blocked by the gas check valve 215 and communicates via a pneumatic pathway 227 to the gas-side reservoir 171. The membrane 175 separates driving gas pressure from the fluid, which sits in the fluid side-reservoir 172. The cassette body 220, cassette top 222, and cassette bottom 225 provide fluid tight sealed pathways. The bypass screw 265 normally blocks free flow between the inlet tube 180 and the outlet tube 190. The gas filter 216 sits between the fluid-side reservoir 172 and the gas check valve 215. FIG. 7b shows a cross-sectional view of the inlet valve 135 and the outlet valve 145.

Referring to FIG. 7a, the membrane 175 creates a fluid/gas barrier. Fluid occupies the fluid-side reservoir 172, between the inlet valve 135 and the outlet valve 145, which are each one-way valves, allowing flow of fluid in only one direction from inlet tube 180 to outlet tube 190. The fluid held in the fluid-side reservoir 172 is kept segregated from the gas-side reservoir 171 via the membrane 175. If the membrane 175 is flexible and freely moving, then the differential pressure across the membrane is negligible. The fluid, while sitting in fluid side reservoir 172, is in contact with a gas filter 216, for active air elimination, as described above.

Referring to FIG. 7b, the inlet valve 135 and the outlet valve 145 are symmetrical, both serving as passive check valves on either side of the fluid-side chamber 172. From the fluid-side chamber 172, fluid can be driven by positive pressure through the outlet valve 145 to outlet tube 190, leading to the fluid sink 140. The entire pathway 131 from the source 130 to the sink 140 is sealed and sterile.

FIG. 8 is a cross section of the inlet valve 135. The geometry and function of the outlet valve 145 can be identical, so the same elements apply. The inlet valve 135 is assembled onto the cassette body 220, and then the membrane 175 and cassette bottom 225 are bonded to the cassette body 220 to create a fluid tight seal. Fluid 50 communicates freely with a proximal valve chamber 235. Valve flow channels 237 provide a pathway to a distal valve chamber 236, but the inlet valve 135 prevents flow of fluid because it is sealed at a valve seat 234. A gap is formed and fluid flows at the valve seat 234 from the proximal valve chamber 235 to the distal valve chamber 236 when the pressure differential pressure forces exceed the valve force 242. The valve force 242 is determined by the relative position of a valve retainer 233 and the valve seat 234. The flow of fluid exits the distal valve chamber 236 via the valve inlet channel 238, entering fluid-side reservoir 172.

Referring to FIG. 8, the fluid 50 comes from inlet tube 180 and sits in proximal valve chamber 235, unless the differential pressure, as compared to distal valve chamber 236, is high enough to offset valve force 242 and cause the inlet valve 135 to open. When the inlet valve 135 opens, fluid travels through valve flow channels 237, across valve seat 234 and into distal valve chamber 236. In conditions where pressure is relatively negative in the fluid-side chamber 172, the fluid travels through the valve inlet channel 238.

Pressure in the fluid side reservoir 172 is communicated via the valve inlet channel 238 to the distal valve chamber 236. If pressure in the distal valve chamber 236 is greater than pressure in the proximal valve chamber 235, the forces at the valve seat 234 are increased and the inlet valve 135 remains closed to fluid flow. If pressure in the distal valve chamber 236 is less than pressure in the proximal valve chamber 235, the forces at the valve seat 234 are decreased and inlet valve 135 opens to fluid flow. The force required to open the inlet valve 135 at the valve seat 234 depends on the valve force 242, which for any given material, is a function of the distance between the valve retainer 233 and the valve seat 234. Increasing the gap between the valve retainer and the valve seat increases the valve force, requiring a higher differential pressure between the proximal valve chamber 235 and the distal valve chamber 236 to open the inlet valve 135. The function of the outlet valve 145 can be identical to that of inlet valve 135.

In many pumping applications, the check valve function is attempting to have perfect sealing against reverse flow and minimal forward pressure on the order of 2 inches of water required for full flow. In the present fluid control system, the forward cracking pressures are purposefully high, on the order of 30 inches of water or 1 PSId. This high cracking pressure translates into a substantial dimensional interference at the valve seat 234 and a substantial valve force 242, so that the manufacturing tolerances of the interfering parts do not develop substantial variation in cracking pressures.

FIG. 9 shows a close up cross-sectional view of the center portion of the cassette 210. Positive gas pressure is communicated through the gas sealing ring 212, via the cassette sealing surface 221, and upon the gas check valve 215. Gas valve flow channels 245 are blocked by the gas check valve 215 and no flow can enter towards the fluid-side reservoir 172. A certain level of negative gas pressure can distort the gas check valve 215, allowing flow through the gas valve flow channels 245 from the fluid-side reservoir 172 towards the cassette sealing surface 221. Flow of liquid is stopped by the special physical properties of the gas filter 216, which is interposed between the fluid-side reservoir 172 and the cassette sealing surface 221. The gas filter 216 is formed of a hydrophobic material that allows the flow of gas therethrough but not the flow of liquid. The pressure needed to open the gas check valve 215 and allow flow through the gas valve flow channels 245 is the differential pressure between the cassette sealing surface 221 and the fluid-side reservoir 172. Since the membrane 175 is freely moving, the pressure in the gas-side reservoir 171 is effectively identical to that in the fluid-side reservoir 172.

The fluid 50 is, in practice for an infusion to a patient from a medical pump, a combination of air (the gas) and liquid. Especially during an initial priming function or when changes are made to the source container, quantities of air can appear in the fluid-side chamber 172. During the states CHANGE NEG 823 and FILL 824, negative gauge pressures are created by the linear actuator 115. These negative pressures are seen at the cassette sealing surface 221 and the top of the gas check valve 215. If the fluid-side chamber 172 contains air that is touching the surface of the gas filter 216, then flow of air can travel from the fluid-side chamber 172 to the cassette sealing surface 211 via the gas check valve 215. Unlike the inlet valve 135 and the outlet valve 145, which each have relatively high cracking pressures, the gas check valve 215 has a relatively low cracking pressure and opens easily. If air is contained within the fluid-side chamber 172, but is not touching the surface of the gas check valve 215, then it remains in fluid-side chamber 172. The requirement for detecting this residual air is still important, even though, in most circumstances, an unlimited amount of air can be removed.

Figure 10B:
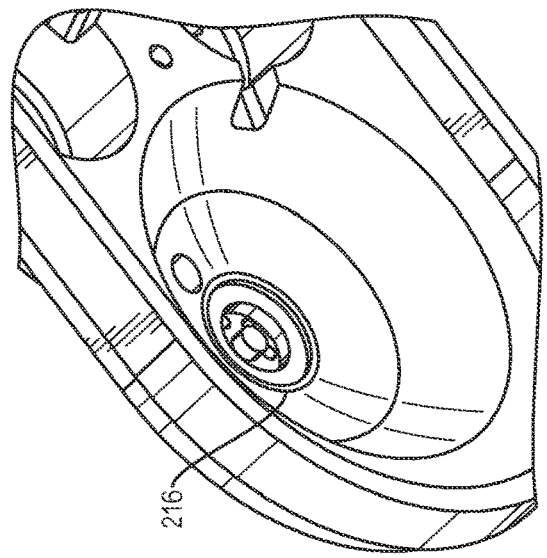
FIGS. 10a and 10b are isometric views illustrating an air filter for an air elimination system used with the cassette.
Figure 10A:
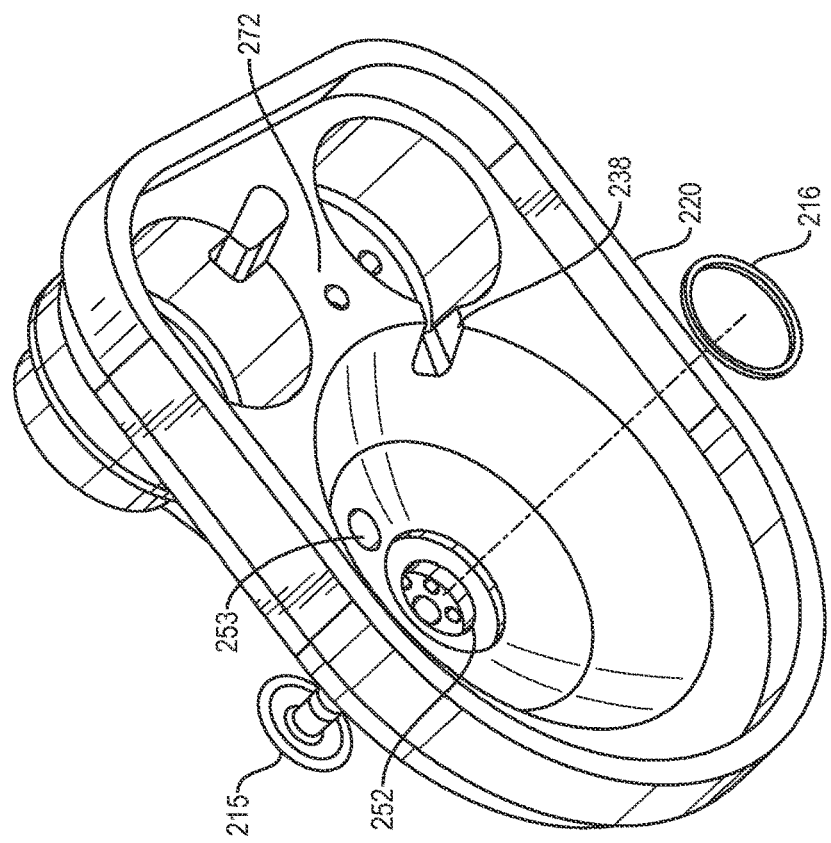

FIG. 10 shows a close up view of the construction of the cassette 210 in the vicinity of the air filter 216. The gas check valve 215 is inserted into the cassette body 220 from the top. The gas filter 216 is fitted into a gas filter seat 252. Fluid sits on top of the membrane 175 in the space of the fluid-side reservoir (not shown in FIG. 10) and exits via the valve outlet channel 253. Fluid enters the fluid-side reservoir 172 via the valve inlet channel 238. FIG. 10b shows the relationship of the gas check valve 215, the cassette body 220, and the gas filter 216 as assembled.

Figure 11A:
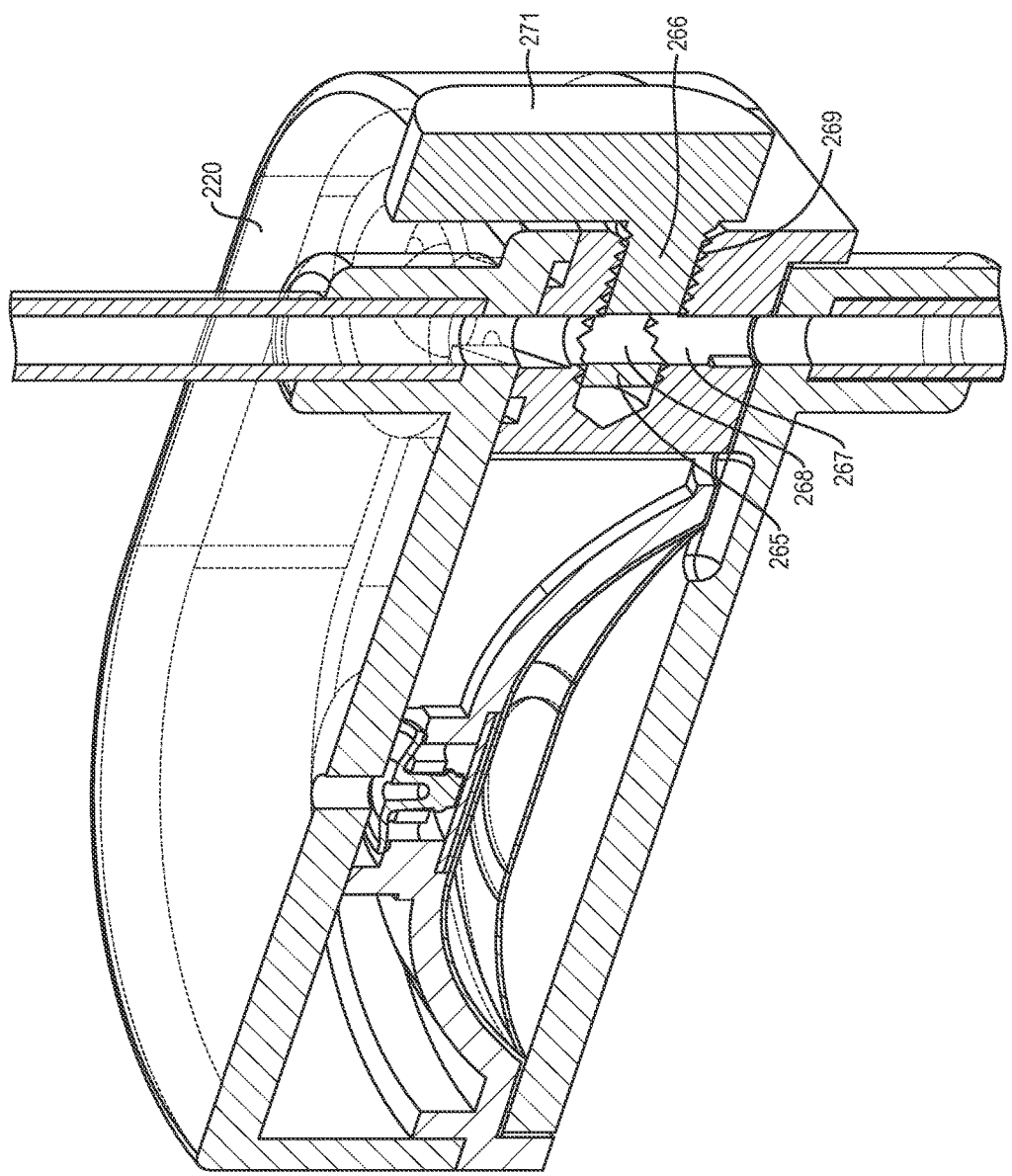
FIG. 11a is an isometric view of a by-pass valve assembly used with the cassette.
Figure 11B:
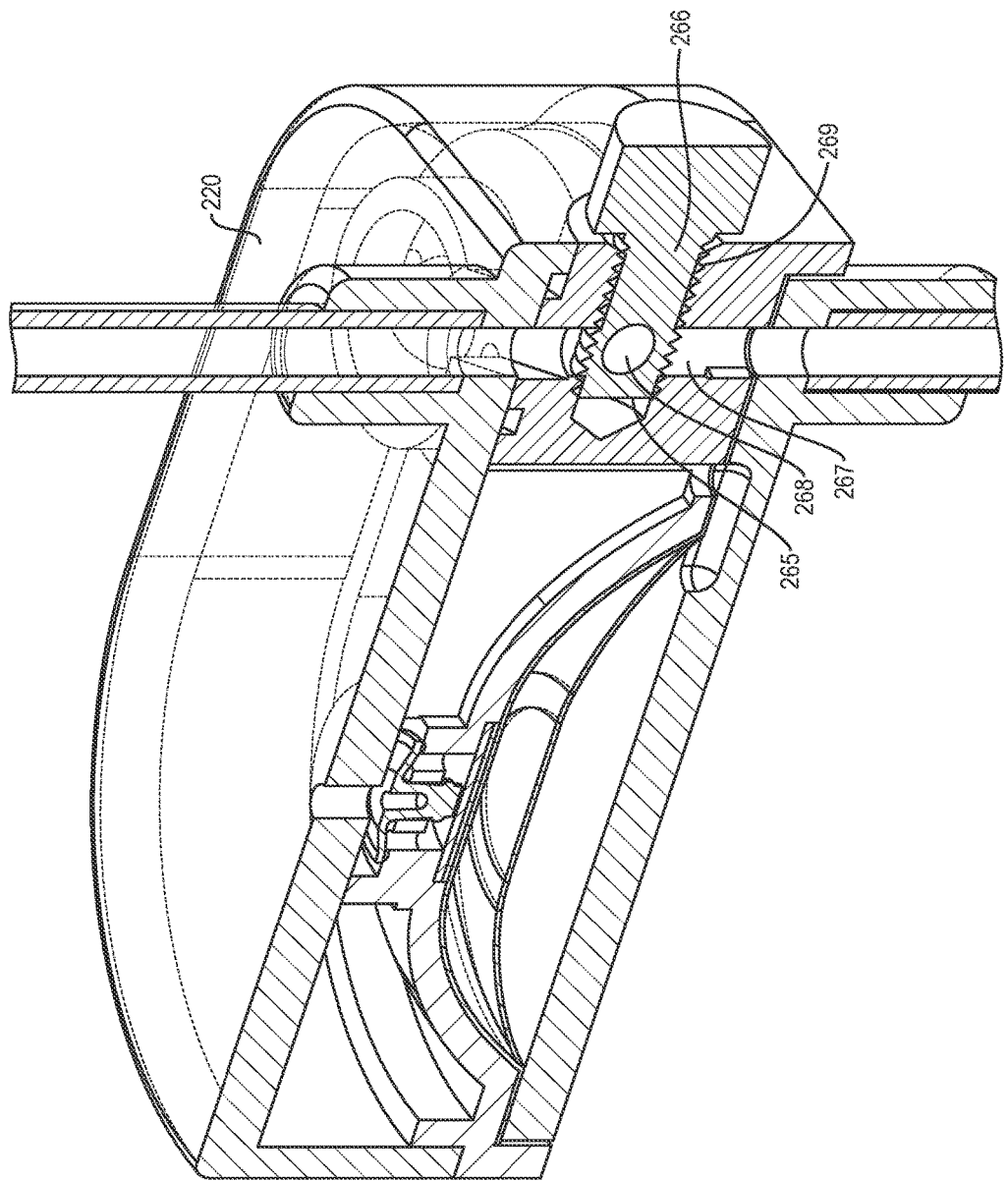
FIG. 11b is an isometric view of the by-pass valve assembly in a closed position.

While the ability to infuse accurately over a wide flow rate range, monitor conditions, and remove air bubbles are useful features of the present system, there may be times when manual control of fluid flow is required. FIGS. 11a and 11b illustrate one form of bypass valve 265 which can open a bypass channel 267 between the inlet tube 180 and the outlet tube 190. The bypass channel 267 is a feature in the cassette 210 which creates a flow path from proximal to the inlet valve 135 to distal of the outlet valve 145. It is normally closed by the bypass valve. The bypass valve includes a screw 266 that fits within an internally threaded aperture 269 in the cassette body 220. The screw can be rotated by a handle 271 protruding from the cassette body 220. An opening 268 is formed through the screw. FIG. 11a shows the bypass valve rotated into the open position, in which the opening 268 is aligned with the channel 267, allowing fluid to flow through the cassette. FIG. 11b shows the bypass valve rotated 90° into the closed position, in which the opening 268 is not aligned with the channel 267. Fluid flow is blocked from the channel 267 and diverted to the inlet valve 135.

FIG. 12a is an exploded view of the cassette 210. Gas pressure communicates through the gas sealing ring 212 and the cassette sealing surface 221 before traversing to a pneumatic pathway 272 in the cassette body 220. A membrane gas passthrough 276 in the membrane 175 allows gas to reach a bottom gas pathway 278 in the cassette bottom 225. The bottom gas pathway 278 communicates to the gas-side chamber 171, allowing the gas pressure to impinge upon the membrane 175 and communicate to the fluid-side chamber 172. FIG. 12b is a top view of the cassette body 220, showing the pneumatic pathway 272. Also visible is the valve outlet channel 281.

A primary requirement of any intravenous pump is to prevent a runaway overinfusion to a patient when the administration set is removed from the pump. The cassette 210 is retained in its relationship to pump housing 260 until the controller 150 goes to the state UNLOCK 821. The user can then remove the cassette 210 from the pump housing 260 and pressure is removed from the gas-side chamber 171.

The head height of the source 130 is limited by the total tubing length of the inlet tube 180 and the outlet tube 190, so the driving pressure is limited to less than 2 PSIg. The inlet and outlet valves 135, 145 operate in series, each with a cracking pressure on the order of 1 PSI, for a total cracking pressure of 2 PSI. In normal application, the driving pressure is far less than 2 PSI, so flow reliably stops and is never in a free flow condition.

One benefit of high cracking pressure check valves is the requirement of significant positive and negative pressures to achieve fluid flow. The cessation of fluid flow to the sink can be achieved by simply relieving the driving pressure. Activation of the vent valve 112 immediately stops fluid flow through the outlet valve 145. While there may be some stored capacitance in the outlet tube 190 that continues to discharge into the sink 140, that value is small due to the typically low operating pressures of system.

FIG. 13 illustrates an embodiment of a failsafe circuit. The vent function is made redundant by the addition of a vent backup valve 512. Activation of either vent 112 or vent 512 reduces the gauge pressure of the gas-side chamber 171 to zero and fluid flow stops. The vent valve 112 is activated by a digital logic circuit of the controller 150 during normal operation. The vent backup valve 512 is operated by capacitive discharge that is held in abeyance by a pulse every second from the controller 150, in response to a regular communication from the host processor 380. If host processor 380 does not successfully communicate with the controller 150 or if the controller 150 is incoherent, then the pulse is not issued to hold up the capacitive discharge and the vent backup valve 512 is activated, even in the event of a total power loss. The vent backup valve 512 can be activated routinely by withholding the pulse, to test the proper operation of vent backup valve 512.

Control of the fluid system is described with more particularity as follows. The measurements made during an infusion can be used to determine the following:
 a) amount of liquid delivered to the sink (patient);
 b) amount of air in the fluid line;
 c) source fluid pressure;
 d) source fluid impedance;
 e) sink (patient) line pressure;
 f) sink (patient) line impedance;
 g) verification of motor movement; and
 h) verification of vent function.

Even though there are a substantial number of characteristics of the fluid flow environment for the system, there are only three parameters to examine, from which all the information is inferred. The pressure signal 322 measures absolute pressures under a query from the controller 150. The second parameter is the position of the linear actuator 115. The use of a stepper motor and home switch provides for an accurate measurement of the linear actuator. Time is the third parameter. Even though the effective flow rate of the system depends on the pressure developed in the reservoir 120 and connected gas-side chamber 171, the controller 150 is not attempting to maintain a certain driving pressure. Pressure generation is a dependent variable in the system.

Each step of the motor provides a known and constant change in gas volume in the system. The resultant change in absolute pressure provides a measurement of the total gas volume. Thus, each step of the motor gives an indication of the fluid volume at any point in time. Changes in fluid volume over time provide an indication of the flow rate. When the reciprocating element is advanced, the pressure driving the fluid first increases and then decreases as fluid leaves the system and "leaks" into the sink. This is illustrated as a stepped or sawtooth shape on a graph of pressure vs. time. (See, for example, FIG. 16.) The change in pressure provides a real time proportional signal related to the fluid flow rate.

The controller uses the ideal gas law to perform many calculations. The ideal gas law states:

$$PV=nRT$$

where: P is the absolute pressure of the gas, and is measured by the pressure sensor;
 V is the volume of the gas and is determined by the number of motor steps;
 n is the number of moles of gas in the volume and is unchanged here;
 R is a universal gas constant; and
 T is the absolute temperature.
The controller compares measurements of pressure and volume at different times:

$$P_1V_1/n_1R_1T=P_2V_2/n_2R_2T_2$$

In this system, n1=n2 and R1=R2 and the absolute temperature T1 and T2 are effectively unchanged in the time intervals measured. The volumes $V_1$ and $V_2$ are the total gas volumes in the reservoir 120, in the cassette and in dead space such as the conduit between the reservoir 120 and the chamber 170. The volume of the reservoir can be determined by calculation. The volume of the dead space is unchanging, and the total contained volume in the cassette is invariant. Thus, the change in liquid volume in the cassette can be computed from this relationship. The pressures $P_1$ and $P_2$ are the measured pressures at two times, which may be before and after a volume change. Thus, the relationship becomes:

$$P_1V_1=P_2V_2$$

Pressure signals collected via pressure transducer 155 demonstrate the changes in pressure in gas reservoir 120 under various conditions. Pressure within the gas reservoir 120 can change under three conditions: first, if the actuator 115 moves within the gas reservoir 120 and changes the gas volume; second, if fluid leaves the fluid-side chamber 172 via the outlet valve 145 to the fluid sink 140; and third, if fluid enters the fluid-side chamber 172 via the inlet valve 135 from the fluid source 130.

Referring to FIG. 14, a pressure response to a known volume reduction (e.g., by moving the reciprocating element 115 a known distance) is shown at A. The pressure is sensed before and after the known decrease in volume, while both the inlet and outlet valves are closed. Signal A is used in calculations leading to a measurement of total gas volume. An example of the calculation of a total gas volume at a time $t_1$ is as follows:

The effective surface area A of the actuator, e.g., a bellows or piston, is fixed at, for example, 1.3 cm². The actuator is moved by the motor from an initial displacement position $D_{init}=1$ cm to a final position $D_{final-1}=2$ cm. The volume change $V_{change}$ while both the inlet and outlet valves are closed can then be calculated as the area times the distance moved:

$$V_{change} = A(D_{init} - D_{final-1}) \quad (1)$$
$$= 1.3 \text{ cm}^2(1 \text{ cm} - 2 \text{ cm})$$
$$= -1.3 \text{ cm}^2$$

The pressure when the actuator is at $D_{init}$ is measured to be $P_{init}$=15 psi, and when the actuator is at $D_{final}$ is measured to be $P_{final-1}$=20 psi. The initial volume $V_{init}$ at time $t_1$ is then calculated as follows:

$$V_{init} = \frac{\frac{V_{ch} P_{final}}{P_{init}}}{1 - \frac{P_{final}}{P_{init}}} \quad (2)$$

$$V_{init} = 5.2 \text{ cm}^3$$

As noted above, the change in pressure of fluid in the fluid-side chamber is equivalent to the change in gas pressure in the gas-side chamber. Thus, the fluid volume change can be calculated by calculating the total gas volume at two different times using Equations 1 and 2 above. For example, at time $t_2$, the actuator is again moved 1 cm for a volume change $V_{change-2}$=−1.3 cm$^3$. The pressures before and after moving the actuator are measured to be $P_{init}$=15 psi and $P_{final-2}$=19.5 psi. Using Equation 2, the total gas volume is calculated to be 5.63 cm$^3$. The difference between the gas volumes at $t_1$ and $t_2$ is:

$$5.65 \text{ cm}^3 - 5.2 \text{ cm}^3 = 0.43 \text{ cm}^3$$

This value is used to increment the cumulative delivered volume. Knowing the fluid volume change, the amount of fluid delivered to the fluid sink can be accurately monitored using only the pressure measurements coordinated with the known incremental linear movements of the actuator.

Figure 15:
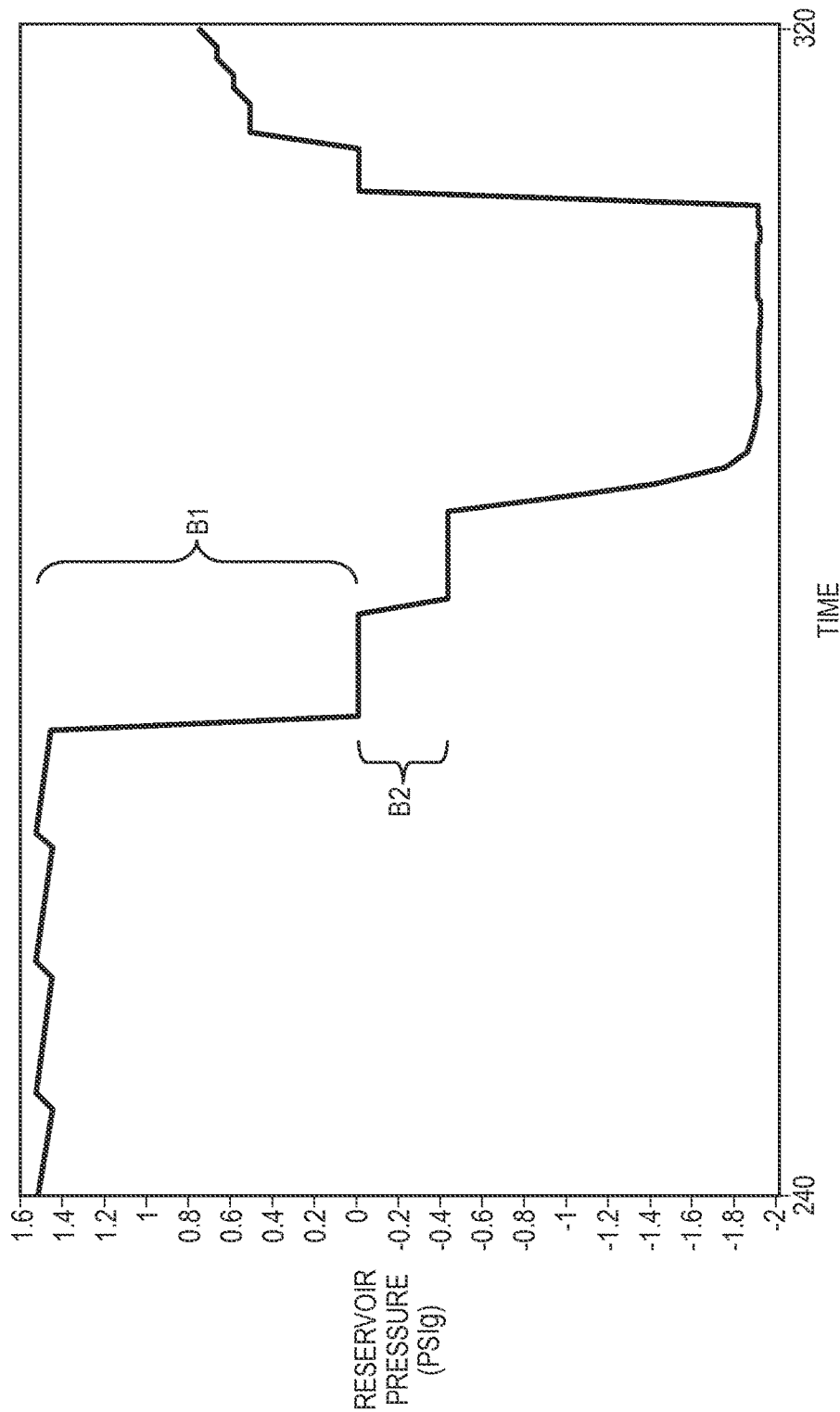
FIG. 15 is a graph of a pressure response to a known increase in gas volume.

Referring to FIG. 15, a pressure response when vent valve 112 is opened is shown as B1. (The pressure returns to 0 PSIg.) A pressure response to a known volume increase is shown as B2 (the vent valve having been closed). Signal B2 is used in calculations leading to a measurement of total gas volume, for example, during a fill cycle, as described in the example above. The pressure is measured both before and after the increased displacement.

Figure 16:
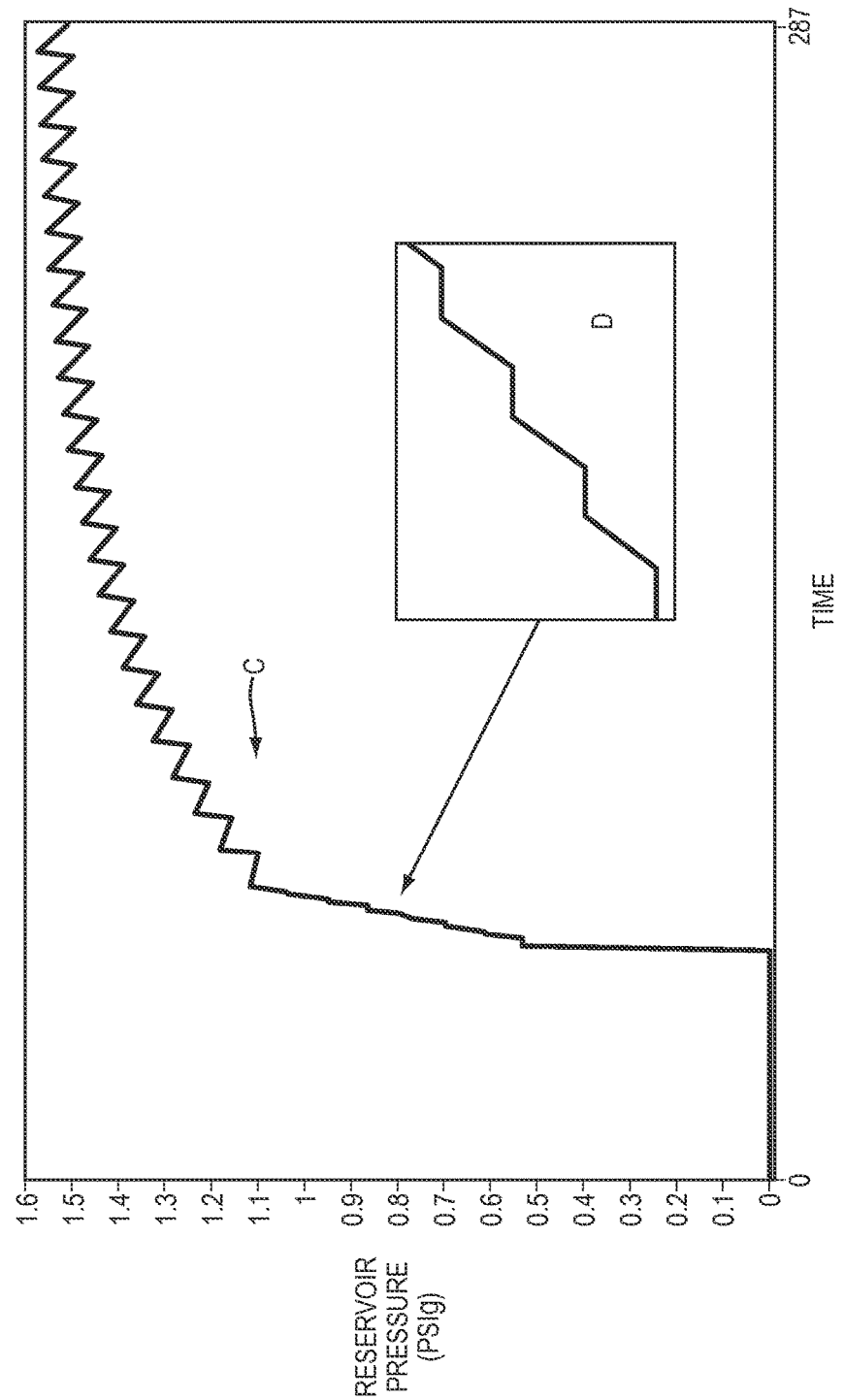
FIG. 16 depicts the change in pressure when a pressure-activated one way valve is opened with increasing pressure.

FIG. 16 illustrates a pressure response to individual incremental movements of the actuator 115, which progressively decreases the gas volume and increases pressure, because the outlet valve is closed. The pressure increase is shown as D. Note that the pressure at D remains unchanged between motor moves, as indicated in the enlarged view of D. Once a sufficient pressure is reached, the outlet valve opens, shown at C, and a pressure decay is measured. As fluid is delivered through the outlet valve, calculations for motor timing are made as indicated in the following example and referring to FIG. 17.

Motor constants are given as follows, based on the geometry of the gas reservoir 120 of the system:

$$\text{MOT}_{mcl} = 17.3 \text{ } \mu L$$

$$\text{MOT}_{stroke} = 88$$

$$\text{VOL}_{def} = 0 \text{ } \mu L$$

Figure 17:
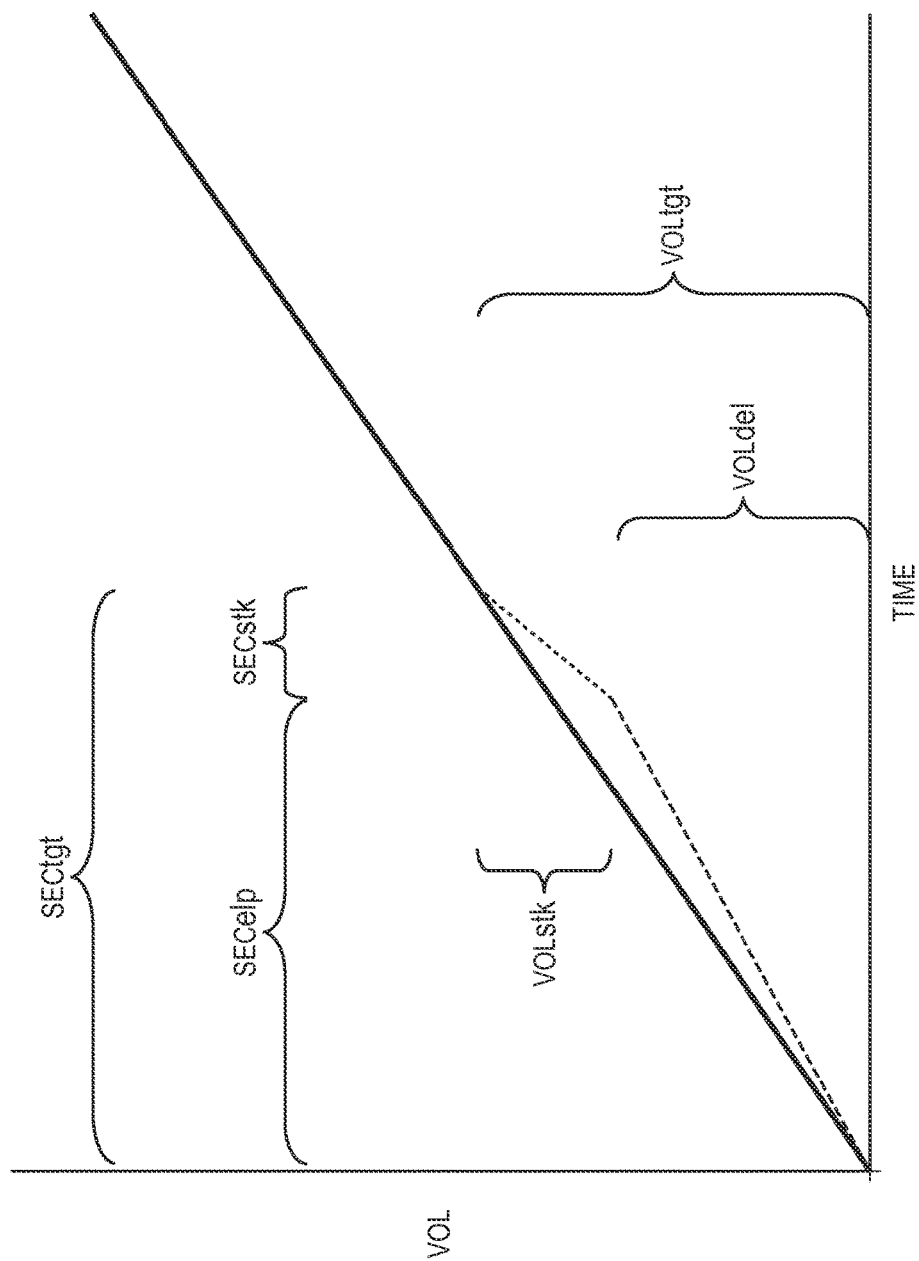
FIG. 17 is a schematic graph of volume vs. time to illustrate flow calculations made during fluid delivery.

$\text{MOT}_{mcl}$ is a calculated constant based on the effective surface area of the bellows or piston times the linear displacement of a single step. $\text{MOT}_{stroke}$ is the number of motor steps taken in a nominal FULL DELIVERY cycle. In FIG. 17, the solid line is the target rate of infusion ($\text{VOL}_{tgt}/\text{SEC}_{tgt}$). The dotted line indicates the actual rate of infusion during the elapsed time from START TIME until TIME NOW ($\text{VOL}_{del}/\text{SEC}_{elp}$). The dashed line is the calculated rate of infusion to meet the target rate. The computation of the target volume, $\text{VOL}_{tgt}$, the amount of liquid to be delivered at the end of the next full stroke, is:

$$\text{VOL}_{tgt} = \text{VOL}_{def} + (\text{MOT}_{mcl} * \text{MOT}_{stroke})$$

The time elapsed since the start of the infusion, $\text{SEC}_{elp}$, (in seconds) is computed as follows:

$$\text{SEC}_{elp} = \text{TIME NOW} - \text{START TIME}$$

which can be converted from mL/hour to µL/sec if necessary as follows:

$$\text{RATE}(\mu L/\text{sec}) = \frac{1000 * \text{RATE}(\text{ml/hr})}{3600 \text{ sec/hr}}$$

The time (in seconds) at which the target volume should be completed, based on the target flowrate, is computed as follows:

$$\text{SEC}_{endstroke} = \text{VOL}_{tgt}/\text{RATE} \text{ } (\mu l/\text{sec})$$

The time in which the next stroke should be complete to achieve the target (in sec) is computed as follows:

$$\text{SEC}_{stroke} = \text{SEC}_{endstroke} - \text{SEC}_{elp}$$

The time, $\text{MOT}_{btwsteps}$, between motor steps (converted to msec) to achieve the rate is computed as follows:

$$\text{MOT}_{btwsteps} = \text{SEC}_{stroke} * 1000/\text{MOT}_{stroke}$$

Figure 18:
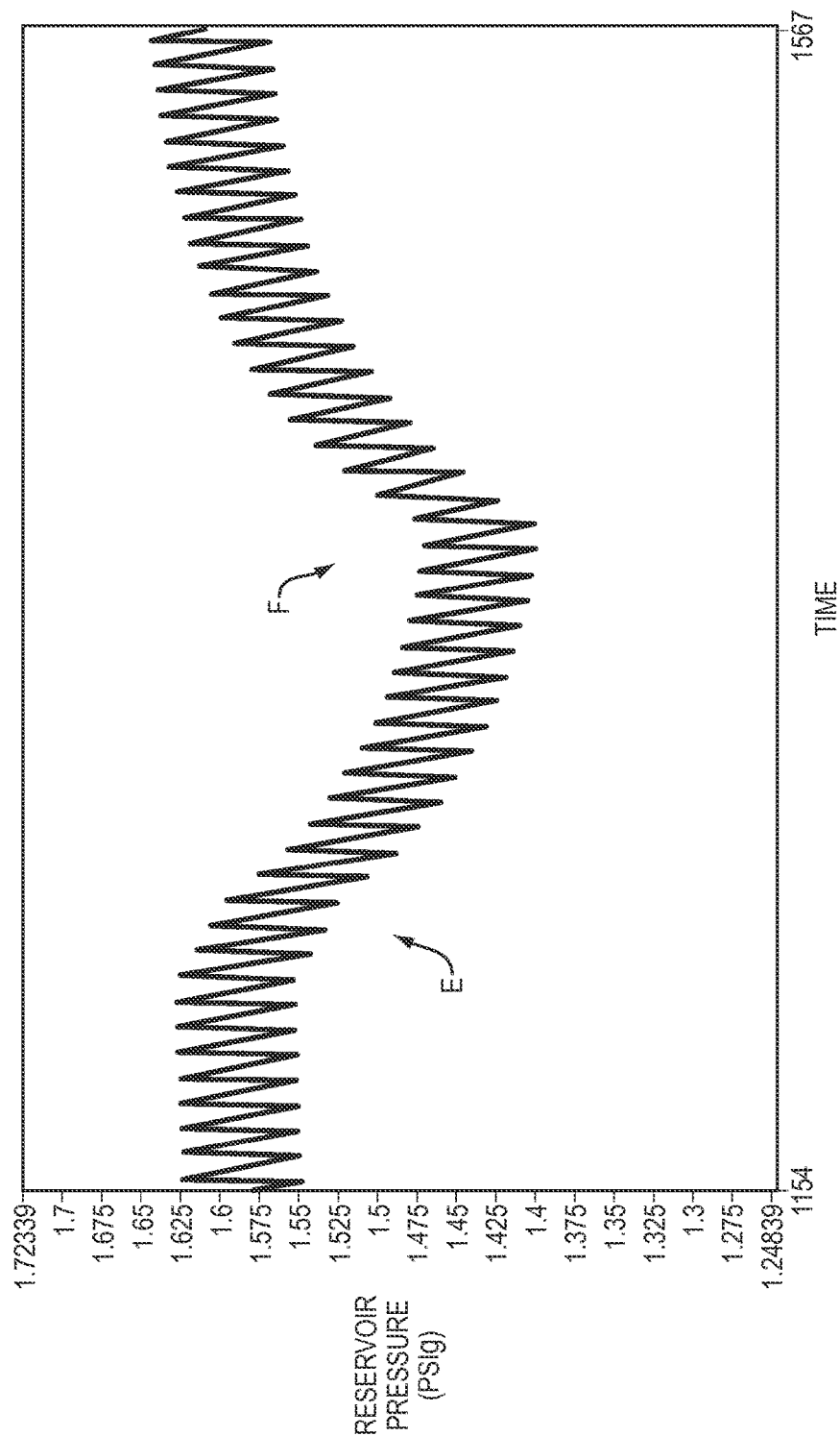
FIG. 18 depicts the change in pressure when the sink pressure changes.

The system is also capable of responding to various conditions that occur during an infusion. For example, FIG. 18 illustrates a possible pressure response when the hydrostatic pressure of fluid sink 140 is changed. Pressure pattern E indicates a reduction in the pressure. Once the system detects the reduction shown by pattern E, the system responds to increase the pressure, indicated by pressure pattern F, which shows the pressure increasing.

Figure 19:
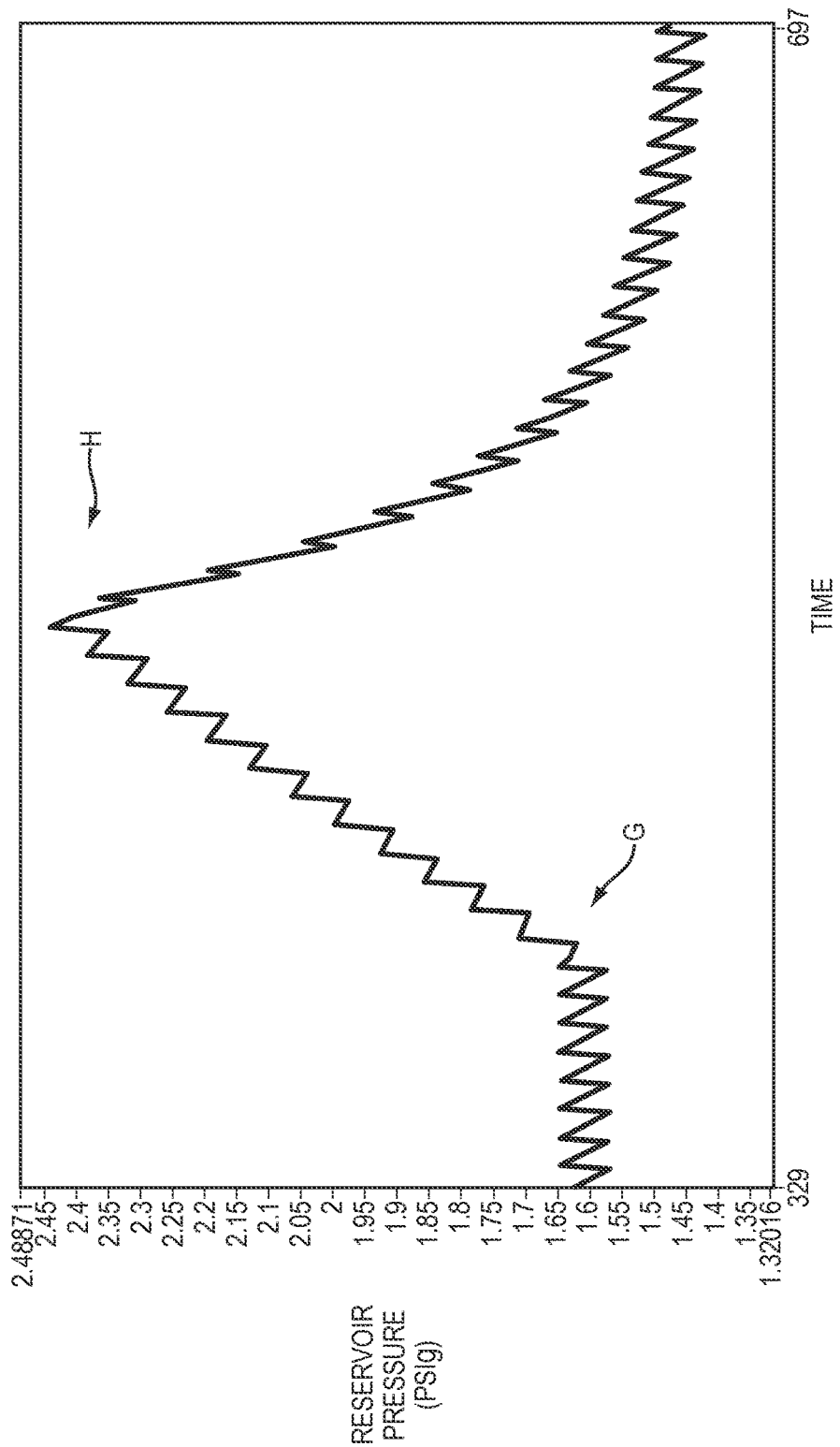
FIG. 19 depicts the change in pressure when the sink impedance changes.

FIG. 19 shows a pressure response when the impedance of the flow into the fluid sink 140 is changed. Pressure pattern G illustrates pressure changes that indicate that the sink impedance is increased. Pressure pattern H illustrates pressure changes that indicate that the sink impedance is reduced.

Figure 20:
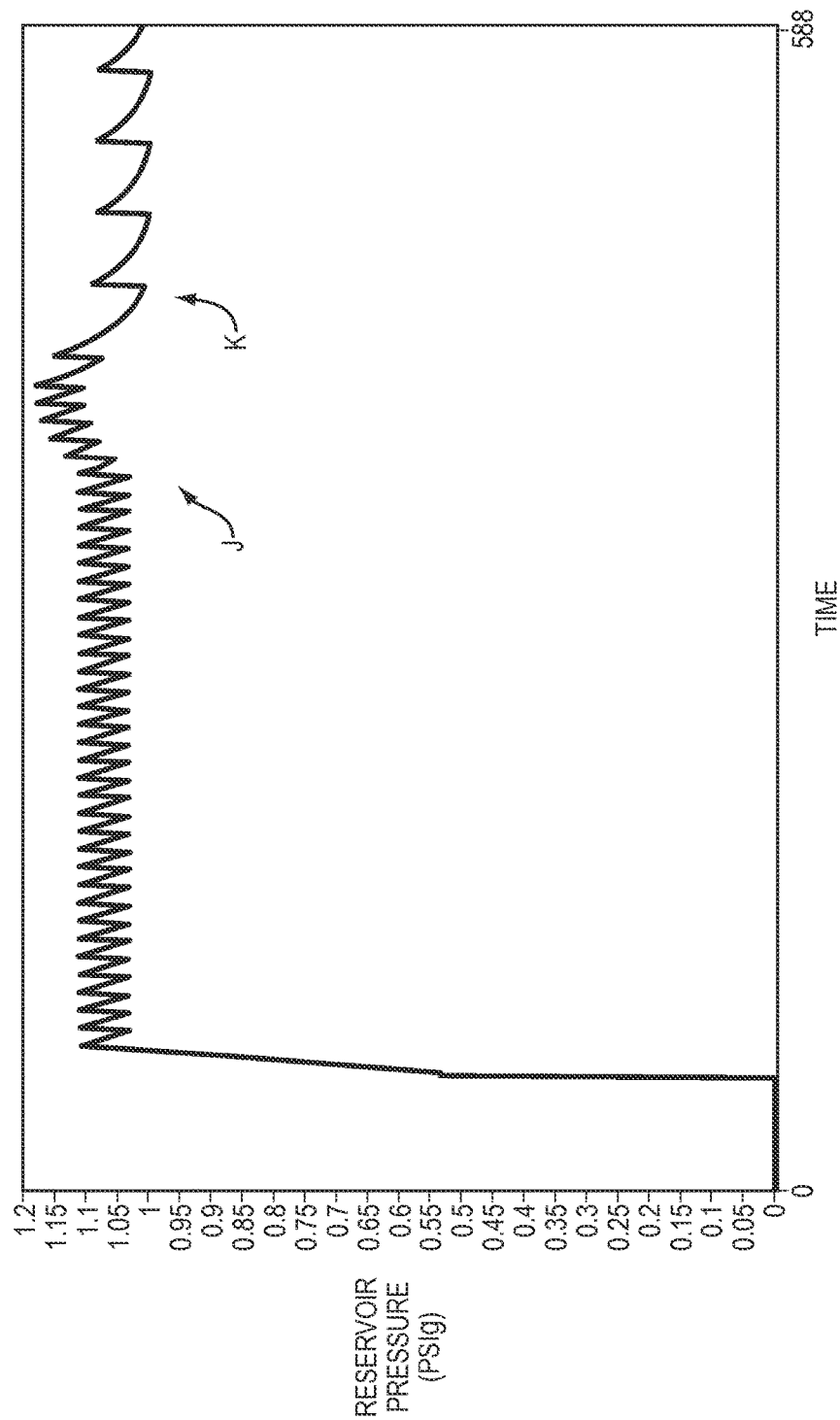
FIG. 20 depicts the differentiation between pressure and impedance changes in the sink.

The system can distinguish between impedance changes and changes in sink pressure. Referring to FIG. 20, a pressure rise is detected, indicated by J. The movements of the actuator 115 are then slowed to better see the baseline pressures, shown at K. In this instance, the baseline pressure does not rise, providing an indication that the pressure rise seen at J results from increased impedance of the fluid flow.

Operation of the controller 150 is further described with more particularity as follows. The parameters measured or calculated by the controller 150 are set out in the following Table:

| | |
|---|---|
| TARGET VOL (µL) | Amount of liquid in micro liters to be delivered; i.e., the target volume of liquid to be delivered |
| TARGET TIME (sec) | Number of seconds in which to deliver TARGET VOL |
| START TIME | Timestamp of when infusion begins |
| OWED VOL (µL) | Volume of liquid remaining in the scheduled infusion |
| DELIVERED VOL (µL) | Volume of liquid measured to have been delivered to the sink |
| STROKE VOL (µL) | Amount of gas contained in known displacement of linear actuator, i.e., volume displaced by a stroke of the linear actuator |

| | |
|---|---|
| TARGET STROKE TIME (msec) | Time at which next STROKE VOL should be delivered |
| MOTOR STEPS | Number of motor steps taken for complete STROKE VOL |
| STEP TIME (msec) | Timing between motor steps |
| DELIVERED VOL FULL | Amount of complete STROKE VOL delivered, i.e., cumulative volume of liquid delivered; incremented after each state DELIVER |
| DELIVERED VOL INTERIM | Portion of a single STROKE VOL delivered, i.e., the volume delivered in an ongoing state DELIVER; reset to 0 after each state DELIVER is completed |
| MOTOR COUNT | Number of MOTOR STEPS taken |

The host processor 380 sends to the controller 150 (or the controller calculates based on user inputs) two variables. TARGET VOL is a measurement of microliters of liquid to be delivered to the fluid sink 140 over a period of TARGET TIME starting from the time of the communication, START TIME.

Measurement of DELIVERED VOL, the volume of liquid delivered to the sink, is a primary parameter for calculating the target delivery, TARGET VOL. There are two components to this measurement, the first being DELIVERED VOL FULL, the tally of completed states of the state DELIVER 827. The second component, DELIVERED VOL INTERIM is the estimate of fluid delivered in the midst of a single ongoing state DELIVER 827. Once each state DELIVER 827 has been completed, DELIVERED VOL INTERIM is set to zero and DELIVERED VOL FULL is incremented. Over multiple cycles, the accuracy of DELIVERED VOL INTERIM becomes less relevant, although still important for low flow rates which may deliver a single STROKE VOL over many hours. DELIVERED VOL INTERIM may be computed in two ways. Under most conditions, the number of steps taken during the state DELIVER 827, the MOTOR COUNT divided by MOTOR STEPS provides a good estimate of the percentage completion of STROKE VOL. For example:

If MOTOR COUNT=100,

MOTOR STEPS=400, and

STROKE VOL=1,000 µl, then DELIVERED VOL INTERIM=(100/400)*1000=250 µL.

The controller 150 invokes another precision volumetric method to compute DELIVERED VOL INTERIM at flow rates substantially below 5 mL/hr. This measurement should be made on the order of every 10 minutes, so as to eliminate effects of ambient temperature or pressure changes. Instead of the normal single increment of MOTOR COUNT, the controller 150 directs the motor 110 to conduct ten reverse steps, followed by ten forward steps, bringing the linear actuator 115 back to its original position. The reason for making multiple steps with a net zero change in driving pressure is to provide a large pressure signal, needed for a high resolution volume measurement. Recordings of the pressure signal 322 are made at a frequency on the order of 1,000 Hz and stored for analysis. Ideal gas law calculations are used to compute the remaining volume of the fluid-side chamber 172, as described above. Subtracting that volume from the volume at the state FILL 824 provides a value for DELIVERED VOL INTERIM that is not subject to drift or signal to noise ratios.

Referring to FIG. 3, positive pressure generation to move fluid across the outlet valve 145 to the sink 140 is done during only one state, the state DELIVER 827. Assume, for the moment, that the membrane 175 is in a position so that the fluid-side chamber 172 is at a maximum value and is fully filled with liquid and that the gas-side chamber 171 is at a minimum value. Assume also that linear actuator 115 is in the position POS CRACKING 813. At this point of control, any steps forward of the linear actuator 115 actually deliver fluid the fluid sink. (See also point C in FIG. 16.) The controller 150 has moved from the state CHANGE POS 826 to the state DELIVER 827.

At the initiation of the state CHANGE POS 826, the controller 150 computes a value for OWED VOL, calculated by:

OWED VOL=(NOW−START TIME)*(TARGET VOL/START TIME)

The controller 150 keeps track of the volume delivered to the sink, DELIVERED VOL.

The system is designed with a fixed STROKE VOL. To achieve a flow rate error of zero, within the resolution of measurements, the next STROKE VOL should be delivered in TARGET STROKE TIME (converted to msec), calculated by:

$$\text{TARGET STROKE TIME} = \frac{(\text{DELIVERED } VOL - \text{OWED } VOL + \text{STROKE } VOL)}{\text{TARGET } VOL *} $$

$$\text{TARGET TIME}/(1000\ msec/\text{sec})$$

The motor drive has a well-defined mechanical linkage, such that the number of steps to achieve STROKE VOL is exactly known as MOTOR STEPS. The timing between MOTOR STEPS is STEP TIME, as calculated by:

STEP TIME=TARGET STROKE VOL/MOTOR STEPS

Examples

| | | | | | | |
|---|---|---|---|---|---|---|
| reference value | FLOW RATE mL/hr | 60 | 60 | 60 | 6 | 600 |
| reference value | DURATION min | 120 | 120 | 120 | 120 | 240 |
| sample data | NOW | 13:30:00 | 13:30:00 | 13:30:00 | 13:30:00 | 13:30:00 |
| sample data | START_TIME | 12:30:00 | 12:30:00 | 12:30:00 | 12:30:00 | 12:30:00 |
| sample data | TARGET VOL (µL) | 120,000 | 120,000 | 120,000 | 12,000 | 2,400,000 |
| sample data | TARGET TIME (sec) | 7,200 | 7,200 | 7,200 | 7,200 | 14,400 |
| calculated | OWED VOL (µL) | 60,000 | 60,000 | 60,000 | 6,000 | 600,000 |
| sample data | DELIVERED VOL (µL) | 60,000 | 59,500 | 61,000 | 5,990 | 600,000 |
| reference value | ERROR % | 0.00% | −0.83% | 1.67% | −0.17% | 0.00% |
| sample data | STROKE VOL (µL) | 1,000 | 1,000 | 1,000 | 1,000 | 1,000 |
| sample data | MOTORSTEPS | 400 | 400 | 400 | 400 | 400 |

| | -continued | | | | | |
|---|---|---|---|---|---|---|
| calculated | TARGET STROKE TIME (msec) | 60,000 | 30,000 | 120,000 | 594,000 | 6,000 |
| calculated | STEP TIME (msec) | 150 | 75 | 300 | 1,485 | 15 |

During the state DELIVER 827, the motor drive operates forward every TARGET STROKE TIME. If the fluid is leaving the fluid-side chamber 172 at the same rate as the gas-side chamber 171 volume is changing, then there is no change in driving pressure of the fluid.

If the flow of fluid towards the sink is slower than the volume change in the gas-side chamber 171, then the driving pressure increases, causing the flow rate to increase, causing a concurrent increase in flow rate. Similarly, if the flow of fluid towards the sink is faster than the volume change in the gas-side chamber 171, then the driving pressure decreases, causing the flow rate to decrease, causing a concurrent decrease in flow rate.

Following the final step of STROKE VOL, the controller 150 pauses until a pressure signal from the pressure sensor indicates that the outlet valve 145 is closed until moving from the state DELIVER 827 to the state TO MIN 822.

The computation of STEP TIME, the time between steps, is made at the beginning of each state DELIVER 827, so that any delays which occur during any of the other states are automatically compensated for. During the state DELIVER 827, the fixed delivery speed creates an automatic adjustment of driving pressure, within limits, to adjust to changing environmental conditions.

The described system and method represent a simplified computational scheme that works over a large flow rate range. In addition, the system is operable to determine various operating conditions based on pressure data and trends and can provide a notification or alarm to a user if necessary.

Figure 21:
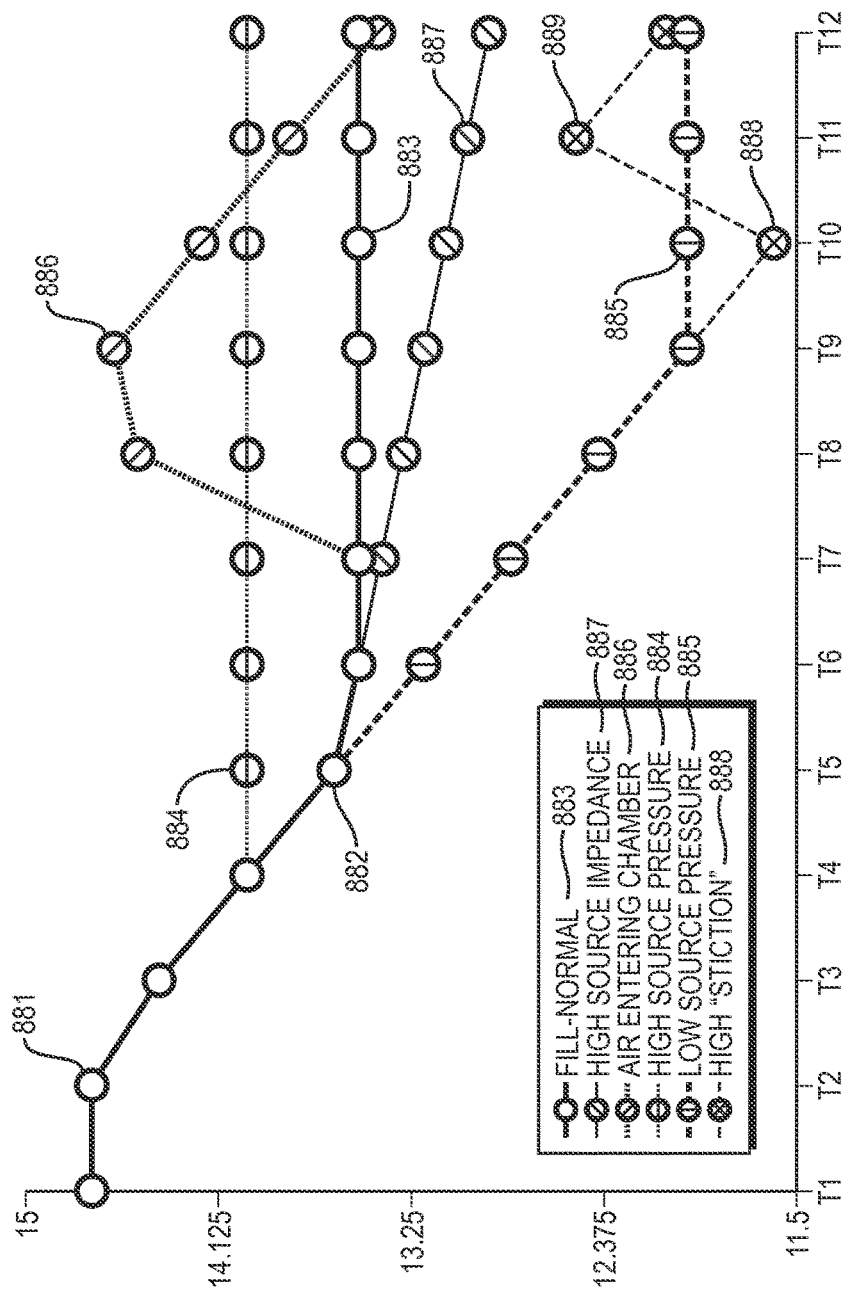
FIG. 21 depicts pressure responses over time during various conditions during a fill cycle.

Referring to FIG. 21, the pressure signals 322 are recorded and analyzed during state CHANGE NEG 823 and state FILL 824 to provide information about various conditions. Information about the fluid source 130 can be discovered by examining the various features of the pressure signals, including the pressure trend 881 before the FILL state commences. A normal cracking pressure of the inlet valve is indicated at 882 and a normal FILL pressure trend is indicated at 883. A high cracking pressure for the inlet valve is indicated at 884. A low cracking pressure is indicated at 885. If air enters the chamber, the pressure response appears as shown at 886. A high impedance in the fluid source is indicated by the trend 887. A pressure response due to stiction followed by release, for example, for a syringe source, is indicated at 888 and 889.

Figure 22:
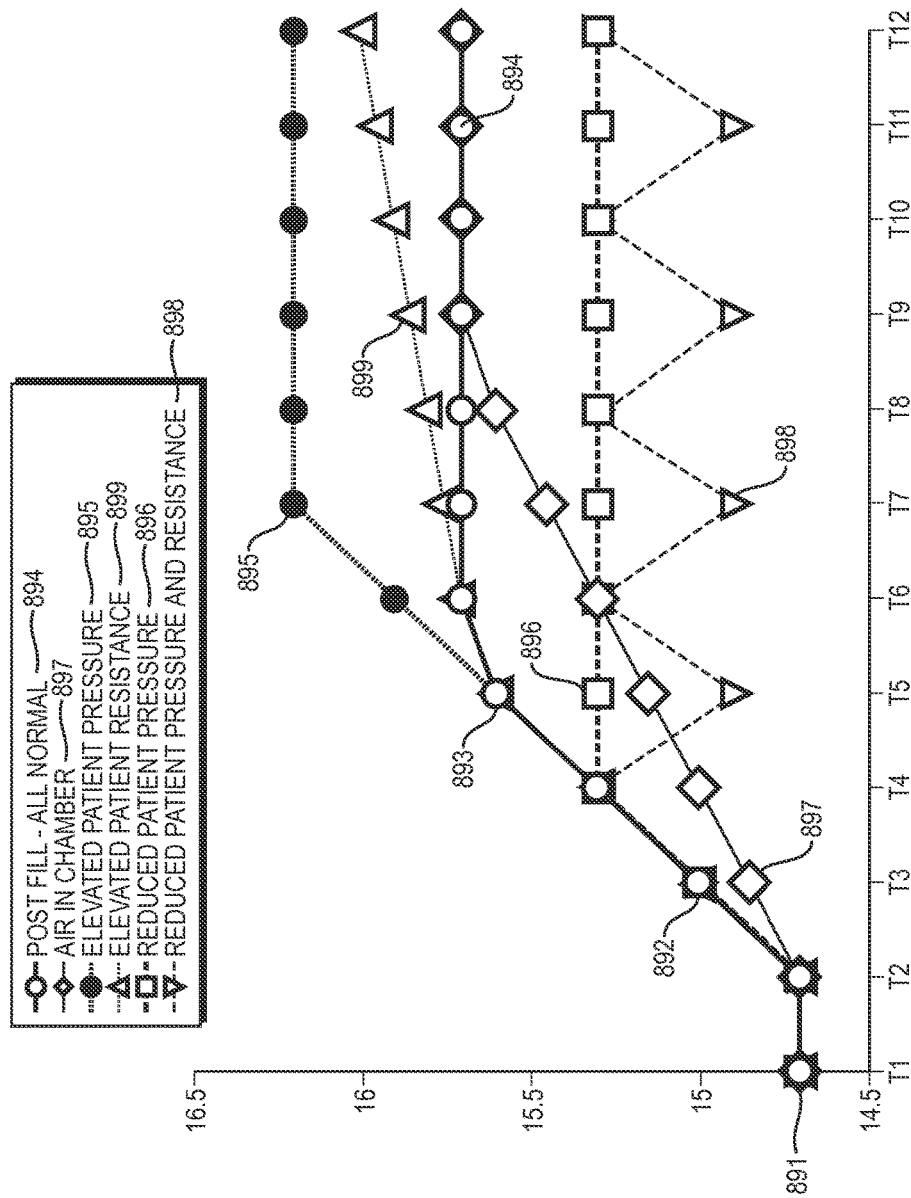
FIG. 22 depicts pressure responses over time during various conditions during a delivery cycle.

Referring to FIG. 22, the pressure signals 322 are also recorded and analyzed during state CHANGE POS 826 and state DELIVER 827. Information about the fluid sink 140 can be discovered by examining the various features of the pressure signals, including the pressure trend 891 before the DELIVER state commences and a normal pressure trend 892 before the outlet valve opens. A normal cracking pressure of the outlet valve is indicated at 893 and a normal DELIVER pressure trend once the outlet valve opens is indicated at 894. A high cracking pressure for the outlet valve is indicated at 895. A low cracking pressure is indicated at 896. If air is present, the pressure response appears as shown at 897. A pressure response indicating a disconnect is indicated at 898. An impedance is indicated at 899.

Even though the system provides a mechanism to actively remove air from the fluid, it does not remove the obligation to measure the presence of air, so that mitigating action can be taken by the user. Assume that the state FILL 824 is complete because volume measurements during the state FILL 824 have confirmed that the gas-side chamber 171 is at its minimum value. After the controller 150 directs the linear actuator 115 to the position MAX 812 in the state TO MAX 825, it moves to the state CHANGE POS 826. A certain number of steps is made, such that a large pressure change is seen, but not enough to open the outlet valve 145. Using the same ideal gas law calculations described above, the total gas volume is calculated and compared to the expected gas volume at the initiation of the state DELIVER 827. Residual gas in the gas-side chamber 171 appears as an incremental total gas volume.

The total gas volume is calculated when the fluid-side chamber is completely filled with liquid. The area A of the actuator, e.g., a bellows or piston, is fixed at, for example, 1.3 cm$^2$. The actuator is moved by the motor from an initial position $D_{init}$=1 cm to a final position $D_{final-1}$=1.2 cm. The volume change $V_{change}$ while both the inlet and outlet valves are closed can then be calculated as the area times the distance moved:

$$V_{change} = A(D_{init} - D_{final-1}) \quad (1)$$
$$= 1.3 \text{ cm}^2(1 \text{ cm} - 2 \text{ cm})$$
$$= -0.26 \text{ cm}^3$$

The pressure when the actuator is at $D_{init}$ is measured to be $p_{init}$=15.000 psi, and when the actuator is at $D_{final}$ is measured to be $P_{final-1}$=17.000 psi. The initial volume $V_{init}$ at time $t_1$ is then calculated as follows:

$$V_{init} = \frac{\frac{V_{ch} p_{final}}{p_{init}}}{1 - \frac{p_{final}}{p_{init}}} \quad (2)$$

$$V_{init} = 2.210 \text{ cm}^3$$

The same calculation done when the chamber contains a 50 µL air bubble is as follows. At time $t_2$, the actuator is again moved 1 cm for a volume change $V_{change-2}$=−0.26 cm$^3$. The pressures before and after moving the actuator are measured to be $p_{init}$=15 psi and $P_{final-2}$=16.950 psi. Using Equation 2, the total gas volume is calculated to be 2.260 cm$^3$. The difference between the gas volumes at $t_1$ and $t_2$ is:

$$2.260 \text{ cm}^3 - 2.210 \text{ cm}^3 = 0.05 \text{ cm}^3 = 50 \text{ } \mu L$$

The simplicity of this measurement demonstrates another benefit of high cracking pressure check valves, providing a significant quiescent period between filling and delivery of the fluid-side chamber 172.

A secondary measurement of air ingress into the fluid-side chamber 172 is made during the state FILL 824. In a liquid filled column, each motor step generates a specific pressure change. The instant that air hits the inlet valve 135, the flow resistance changes by an order of magnitude and the pressure changes diminishes greatly. This measurement of air ingress need not be quantitative, but it serves as a flag to indicate that the subsequent air measurement is important. Referring to FIG. 21, the pressure response at 886 shows the characteristic pressure changes seen during air ingress.

Measuring the hydrostatic pressure of the source 130 is useful. It can often be a determinant of the remaining liquid in a flexible bag hanging above the pump. Upon completion of the state DELIVER 827, the state TO MIN 822 begins, leading to the state CHANGE NEG 823. Increasing negative gauge pressure is developed during the state CHANGE NEG 823 with each motor step. The controller 150 is monitoring the pressure after each motor move to determine a time when the pressure begins to become less negative at the position NEG CRACKING 814, indicating the opening of the inlet valve 135. The pressure at which the inlet valve opens varies with the pressure of the source. The differential cracking pressure of the inlet valve 135 depends upon the valve force 171, which is high. That offset does not, however, prevent the measurement of pressure at the source with high resolution. The valve force 171 is a value roughly known by design and represents pressure at the position NEG CRACKING 814. If the source has a head height of zero, then the inlet valve 135 opens at the expected pressure based only on the valve force 171. If the position NEG CRACKING 814 happens at a less negative pressure, then the source head height can be calculated as a positive head height differential. The actual value of the source head height can only be determined if the host processor 380 exploits its user interface to direct the operator to place the source at an exact head height. Even without quantitative information, the source pressure can be roughly calculated and can be tracked with as much precision as the controller 150 circuitry allows, for example, to a fraction of an inch of water.

It can useful to roughly measure the impedance or resistance to flow from the source during the state FILL 824. This use of the source impedance is the recognition of an upstream occlusion. One of the unique properties of the system is its ability to fill the fluid-side chamber 172 completely even in the presence of a partial upstream occlusion. It may take a relatively long time to complete the state FILL 824 and that would take a toll on the maximum achievable flow rate, but the filled condition of the fluid-side chamber 172 is measured, not assumed. During the state FILL 824, the motor 110 moves at a constant rapid speed, producing a continuous change in negative pressure seen in the reservoir 120. The slope of this pressure change is a direct measurement of the impedance of the fluid as it drags across the inlet valve 135. As noted above, FIG. 21 shows examples of different resistances to flow. A high resistance caused by a viscous fluid would show a steep, continuous slope, as shown at the pressure response 887. Erratic frictional forces from a source incorporating a syringe would show high slopes interrupted by low slope segments during movement of the syringe plunger as shown at the stiction pressure response 888 followed by the release pressure response 889.

Measuring the hydrostatic pressure of sink 140 is useful. It can often be a determinant of a downstream occlusion. Upon completion of the state FILL 824, the state TO MAX 825 begins, leading to the state CHANGE POS 826. Increasing positive gauge pressure is developed during the state CHANGE POS 826 with each motor step. The controller 150 is monitoring the pressure after each motor step to determine a time when the pressure begins to become less positive at the position POS CRACKING 813, indicating the opening of the outlet valve 145. The pressure at which the outlet valve 175 opens varies with the pressure of the sink 140. The cracking pressure of the outlet valve 175 depends upon the valve force 171, which is high. That offset does not, however, prevent the measurement of pressure at sink 140 with high resolution. The valve force 171 is a value roughly known by design and represents pressure at the position POS CRACKING 813. If sink has a head height of zero, then the outlet valve 174 opens at the expected pressure based only on the valve force 171. If the position POS CRACKING 813 happens at a less positive pressure, then the sink head height can be calculated as a negative head height differential. The actual value of the sink head height can only be determined if the host processor 380 exploits its user interface to direct the operator to place the sink at an exact head height. Even without quantitative information, the sink pressure can be roughly calculated and can be tracked with as much precision as the controller 150 circuitry allows, for example, to a fraction of an inch of water.

Figure 23:
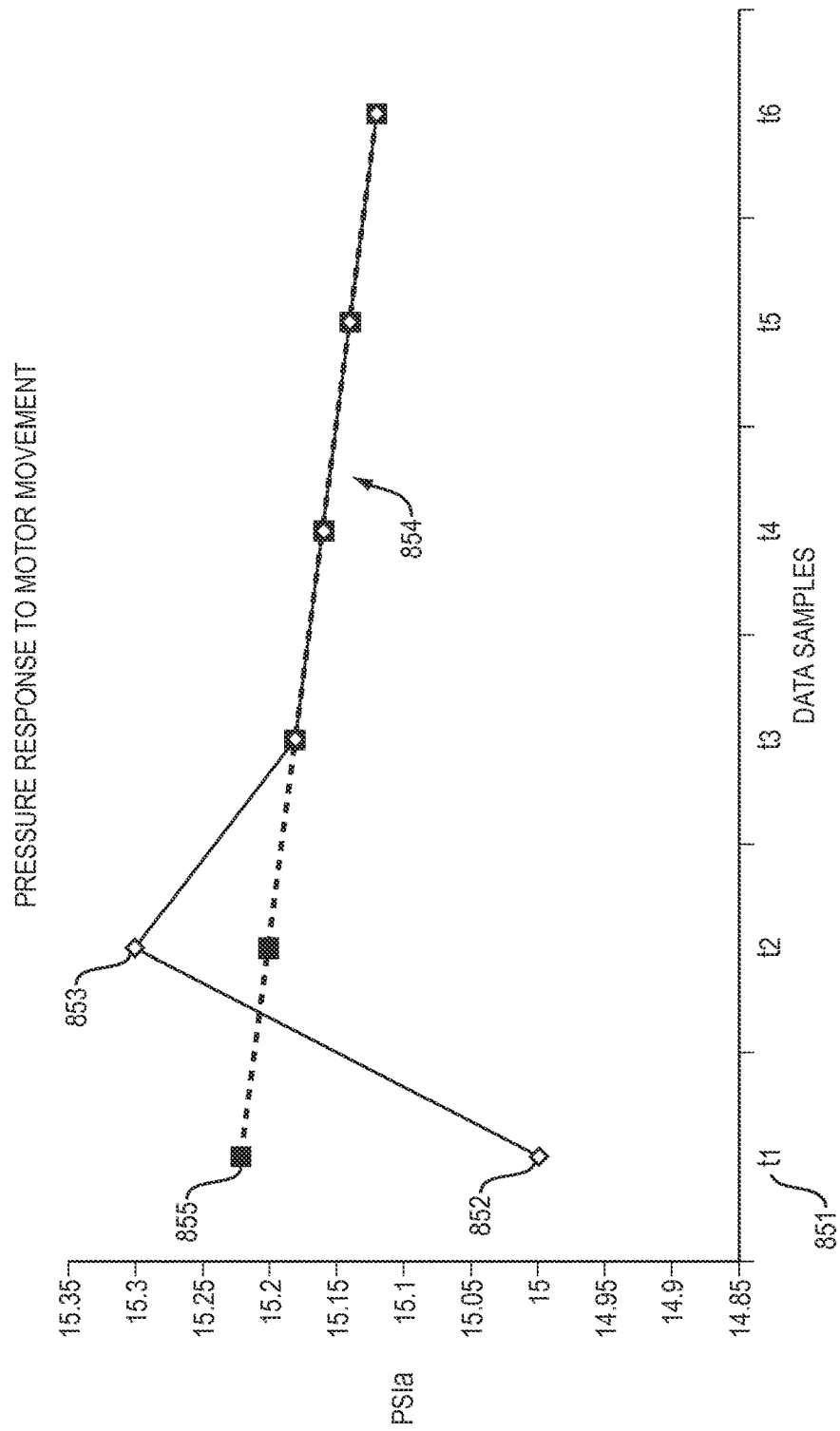
FIG. 23 depicts a pressure response over time during a portion of a fluid delivery stroke.

The measurement of output impedance is not as straightforward as it is for the input described above. Each motor movement during the state DELIVER 827 increases the driving pressure and, so long as the pressure of the fluid-side chamber 172 is enough to open the inlet valve 170, a pressure decay can be measured using the pressure signal 322. During the state DELIVER 827, pressure immediately following each motor step can be recorded for a relatively short period on the order of 100 msec. FIG. 23 shows a method of data sampling during flow during a step of the motor when the resistance of the outlet valve 175 is at it minimal value. The slope of fluid flow can be easily measured from the pressure post trend indicated at 854. The pressure decay, shown by the pressure post trend 854, can be scaled by the pressure differential between the pressure post intercept 855 and at the position POS CRACKING 813 indicated at 852. This measurement provides a calculation of total output impedance, which includes the sum total of resistance across the outlet valve 145, flow resistance of outlet tube 190, flow resistance of any connections, catheters that are interposed between outlet valve 145 and the vasculature of the patient. Significant changes in the output impedance can be suggestive of a clinical problem. Referring again to FIG. 22, the pressure deliver impedance indicated at 899 illustrates a high level of patient resistance. The pressure response disconnect indicated at 898 illustrates the opposite condition of low resistance and low pressure, likely due to a line disconnection.

More particularly, using the ideal gas law, the instantaneous flow rate calculation is made routinely, for example, on the order of once per second, by analyzing the trend of pressure signals 322 transmitted by the pressure sensor. A single value for pressure is derived from an array of samples taken on the order of 1 KHz, so as to analyze the signals for noise.

Referring again to FIG. 23, the pressure signal 322 is recorded before, during, and after each movement of the reciprocating element 115 at time intervals indicated at 851 during a DELIVER step (state DELIVER 827). Subsequent measurements are analyzed for the pressure post trend, indicated at 854, and the pressure post intercept value (also called $P_f$ in the calculations below), indicated at 855, is derived from this trend. The pre motor step pressure, indicated at 852, (also called $P_i$ in the calculations below) is compared to pressure post intercept value 855 using the ideal gas law. The post motor step peak pressure signal, indicated at 853, which is recorded immediately after the movement of the reciprocating element 115, is a thermal artifact form adiabatic contraction that is not included in the calculation.

Assume for this example the following:

Total stroke volume=1,500 µL (fixed by the system)

Steps per total stroke=400 (fixed by the system)

Volume per step in stroke=1,500 µL/400 steps=3.75 µL

Also assume for this example that the reciprocating elements moves 5 steps (e.g., from motor step position 140 to motor step position 135). The volume displaced by these 5 steps is:

5 steps*3.75 µL/step=18.75 µL

The volume at the beginning is known from a previous calculation (correct?) and can be taken as, for example, 525.00 µL. The final volume displacement due to this movement is calculated as:

525.00 µL−18.75 µL=506.25 µL

The initial pressure $p_i$ is measured as 15.00 PSIa. The derived final pressure $p_f$ is 15.22. Thus, from the ideal gas law comparison, the system volume $V_n$ of gas at time n is determined as follows:

$$(V_n+V_i)*P_i=(V_n+V_f)*P_f$$

$$V_n*P_i-V_n*P_f=V_f*P_f-V_i*P_i$$

$$V_n*(P_i-P_f)=V_f*P_f-V_i*P_i$$

$$V_n=(V_f*P_f-V_i*P_i)/(P_i-P_f)$$

Thus:

$$V_n = ((506.25\ \mu L * 15.22\ PSIa) - (5.25\ \mu L * 15.00\ PSIa))/$$

$$(15.00\ PSIa - 15.22\ PSIa)$$

$$= 772.2\ \mu L$$

The fluid control system and method described herein are advantageous for a variety of reasons. The system combines the simplicity of a direct drive pump with the high level of sensitivity of a pneumatic drive system by providing a pneumatically coupled, direct drive infusion control system. The system is based on gentle air pressure and is easier to use. Traditionally, pumps have used powerful mechanical elements to deform tubing or move syringes to expel fluid flow from within these structures. The present direct drive mechanism has the advantage of a simple control algorithm in which a drive motor is advanced in known increments with a known stroke volume. Faster flow rates have shorter intervals between motor pulses.

Traditional infusion pump architectures diminish the sensitivity to the underlying fluid flow going to the patient and potentially expose the patient to high pumping pressures. In a tubing pump, for example, the force required to crush the tubing to an occluded state is far larger than the force required to move the fluid. The present system, however, takes the advantage of a simple direct drive mechanism, yet offers the ability to measure the fluid flow outcome and have increased sensitivity to the environmental factors. This concept applies relatively low pressures, similar to or less than those seen with a gravity infusion, to the fluid and the observation of fluid flow can be observed directly. A thin non-permeable membrane separates the driving air pressure from the fluid being delivered and the net force on the membrane approaches zero. The membrane is formed so that no stretching forces are seen by the membrane; it translates freely on one axis in response to any differential pressure, for example, like a loudspeaker.

A precision reciprocating element is moved via a linear actuator, e.g., stepper motor and a precision lead screw or other volume displacement mechanism. The precision from each of the components is inherent in the manufacturing process and does not add cost to the system design. The motor is advanced at an interval that is a function of the targeted flow rate. Each step provides a new measurement of fluid volume and each measurement in between steps provides a change in pressure proportional to fluid flow. In this way, a single measurement system is used in two ways to measure flow rate.

At very low flow rates, the pressure changes are small and eventually run into a signal-to-noise issue. This noise includes environmental changes of temperature and atmospheric pressure. If the single movement of the reciprocating element results in a pressure greater than desired, then an alternative strategy can be employed to measure air volume. Rather than advance the reciprocating element, the reciprocating element can be withdrawn several steps and then returned to the original position, resulting in no net pressure increase. This "net zero" perturbation of air volume can be as large as needed to provide a large signal, well above the noise floor.

Another advantage of the present system is that it allows for an improved strategy for fluid delivery accuracy. Traditionally, a large volume infusion pump will drive a motor mechanism to achieve a certain flow rate. Any errors in this delivery will be additive over time. The present system provides for automatic compensation for delays that are predictable, such as the time to fill the fluid chamber from the source and for errors that are not predictable, such as a temporary and partial upstream occlusion.

The control provided by the present system is based on a desired delivery of discrete fluid volumes over time, rather than a constant flow rate. Even if the user expresses a desire to go at a flow rate indefinitely, that can easily be expressed as a series of volume over time sequences. For example, to the system, a request for 60 mL/hour could appear as 60,000 microliters over 3,600 seconds or 600,000 microliters over 36,000 seconds.

The present system is operable to deliver a known stroke volume and, advantageously, to measure the actual volume in a fluid chamber at the beginning and end of each stroke delivery. At a fixed point in the control algorithm, the system determines at what future time the completion of the next complete stroke volume is due. Once this time is determined, the dwell between steps in the motor to complete the stroke is easily calculated and the pump proceeds with virtually no computational overhead. Delays from any source, predictable or not, are automatically compensated for and errors in flow rate do not contribute to longer term inaccuracies.

Still another advantage of the present system resides in its ability to provide a short term, self-regulating fluid flow control strategy. Traditionally, the creation of a closed loop control system might require a sophisticated and complex control system. This complexity could lead to problems with reliability and with excessive power consumption. The architecture of the flow control system herein allows for the benefits of a timer-based open loop pumping system (simplicity) and the benefits of a closed loop control system (accuracy and responsiveness).

Since the system herein accurately measures liquid volume delivered to the patient and accurately measures time, the amount due the patient at any instant in time can be measured. For example, in certain embodiments, following every FILL cycle of the fluid chamber, the calculation is made of the time desired to empty the chamber. The time between steps is calculated internally. If, for example, the nominal flow rate is 2 mL to be delivered over 60 seconds and the pump starts this cycle in debt to the patient of 0.2 mL, then the normal 2.0 mL cycle should be shortened by approximately 10% or should be completed in 54 seconds. Since the number of steps required to displace 2.0 mL is precisely known, the time between steps is easily determined.

Following a FILL cycle, there is no flow out to the patient until the outlet valve cracking pressure has been met. The calculations of timing are made at the moment that the outlet valve cracking pressure is met following a FILL. This method intrinsically accounts for the intra-cycle delays with no need for complex control calculation.

At the end of an EMPTY cycle, there is sustained flow out to the patient until the driving pressure falls below the outlet valve cracking pressure. The FILL cycle is delayed until this point in the pressure decay. This method intrinsically accounts for the intra-cycle delays with no need for complex control calculation. If the pump is running behind in its rate, then the steps will happen more rapidly and the delivery pressure will intrinsically increase, causing the rate to catch up to the desired rate. This requires no control code at all to make this pressure adjustment. If the pump is running ahead in its rate, then the steps will happen less rapidly and the delivery pressure will intrinsically decrease, causing the rate to slow down to the desired rate. This requires no control code at all to make this pressure adjustment.

A measure of post-fill high compliance provides an indication of one of two conditions. Air may have entered the system from the source. Alternatively, the fill cycle may have been incomplete, as would occur with an occluded inlet or fully evacuated non-vented supply container. The ambiguity of the signal for high compliance can be resolved with repeated fill cycles. Ultimately, even if the problem is unresolved, it leads to the exact same outcome, namely, the cessation of pumping and a notification, such as an alarm, a text message to a user, or like.

Yet another advantage of the present system resides in its ability to measure source fluid pressure and flow resistance as well as sink fluid pressure and flow resistance without additional sensors. Conventional fluid flow controllers are often equipped with multiple pressure transducers which are situated in a way to record the hydrostatic pressure of the source fluid and of the patient line. This method requires separate pressure transducers, careful coupling of the fluid, and, usually, a poor sensitivity of measurement because the fluid is measured across a relatively thick barrier which imposes its own set of forces. The present system measures source fluid pressure and sink line pressure using a single pressure sensor of the system and offers no complexities in the disposable interface to the pump. This measurement comes at essentially no cost and offers nearly perfect sensitivity. The pressure measurement is subject to a significant offset error, but most of the known clinical considerations for an infusion pump are based on trends, rather than absolute values.

The value of pressure and impedance measurements has a combinatorial effect. For example, a source with low pressure and one with high and variable impedance is likely to be a syringe. Another example would be a source of low impedance and steadily decaying source pressure is likely to be a soon-to-be empty fluid bag. A high patient line impedance and unchanging pressure may indicate a kinked tube. Another example would be a low impedance in the patient line and a reduction in patient line pressure, indicating a likely patient line disconnection. Having knowledge of the source fluid and patient line is an important ingredient for a reliable infusion system.

The system is described herein as a basic system, although systems with added functionality are also contemplated. The fluid control system implements a pneumatically coupled direct drive mechanism that can be integrated as a subassembly into a finished medical product that includes additional components or subassemblies, such as a chassis, a power supply, a user interface, clinical information management, and the like.

In a conventional fluid coupled syringe pump, a slight movement of the piston is displacing incompressible liquid, so the instantaneous pressure change is a function of the downstream compliance, including the syringe wall, the tubing, various connectors, and fluid flow losses. In the present system, a step movement of the reciprocating element increases the air pressure, proportional to the rest of the air space in the reservoir and attached space. For example, a 10-microliter movement of the piston into a total gas space of 1,000 microliters will increase the driving pressure by 1% of atmospheric pressure or merely about 0.15 PSI. This pneumatic coupling solves the impedance mismatch problem of prior art pumping systems mentioned above.

The gas pressure is readily measured with a single precise and calibrated pressure sensor. Instead of using a complex routine where active switching valves combine an unknown gas volume with a known gas volume, so that a computed gas volume can be determined, the present system uses the relationship between a reciprocating element movement and a change in volume. A known motor displacement results in a known volumetric displacement, so the resultant gas pressure measurements result in a calculated gas volume. The absence of a separate measurement sequence results in significant improvement over the prior art, because valves, a control chamber, and related calculations are no longer required. The act of generating gas pressure, either positive or negative, also provides a measurement of gas volume. The pumping phase and measurement phase are unified.

The gas pressure is imposed upon a flexible membrane, with a mechanical configuration that creates negligible forces throughout its entire stroke volume. This configuration could include features such as a thin wall and molded-in curvatures, similar to those found commonly in a so-called "rolling sock" diaphragm. Alternatively, the membrane can be thermoformed to the shape of the housing. Therefore, a gas pressure of 1.0 PSI, for example, imposes a nearly identical pressure on the other side of the membrane which is exposed to the sterile fluid pathway. The differential pressure is very low and known by design. This flexible membrane solves one of the problems with peristaltic pumps in their ability to accurately and sensitively read pressures through the relatively thick wall of an extruded tubular pumping segment.

Alternating air pressure, created by the gas reservoir coupled to the reciprocating element, imposes positive and negative gauge pressures on the liquid side of the membrane. Inlet and outlet check valves proximal and distal to this central membrane create a unidirectional pumping action. The system utilizes a pair of passive fluid check valves with purposefully high cracking pressures, for example, on the order of 1 PSId. The passive check valves are an improvement over designs that utilize active valves. The high cracking pressure of the check valves makes for a very reliable design; there is a tradeoff with low cracking pressure and reliability of sealing. Most check valves in the IV therapy market seek to have a cracking pressure measured in a few inches of water, whereas the present system operates an order of magnitude higher. All infusion devices must incorporate a method of preventing "free flow" when the tubing set is removed from the pump mechanism. The combined cracking pressure of the in-series inlet and outlet check valves serves this "flow stop" purpose with no additional mechanism, component, or complexity.

The liquid side stroke volume of the membrane is on the order of 1 mL. The stroke volume of the reciprocating element is about double that, providing the ability to generate positive and negative pressures during the period when both check valves are shut and then still have the stroke capacity to match the liquid side stroke volume. In order to accommodate all ranges of flow and pressure, there are times when the reciprocating element must be moved to a certain location without generating any pressure on the membrane. The vent valve is used to eliminate pressure on the membrane during such movements. The cost, power consumption, and control logic of the vent valve is negligible. During operation, flow can be stopped with the activation of the vent valve. In certain embodiments, a failsafe design can incorporate a redundant vent valve that is activated by control electronics in the absence of an "ALL OK" control signal, although other fail safe designs are also contemplated.

The control system can be designed to integrate with other components, such as a chassis and user interface, to create a finished medical device. The control system can incorporate commercially available parts, including a microcontroller, a bellows or a syringe-like cylinder/piston, a linear actuator motor/gear, a pressure transducer, and a vent valve. Custom embedded controller software, as described herein, can provide the control based on requests from a host computer that is part of the finished medical device. The user interface, communications, and control logic of the host computer that determines the targeted fluid flow rate are common to all infusion pumps on the market and can be encompassed within the scope of embodiments of the present fluid control system.

The present system can employ a cassette-like configuration that is incorporated into a finished IV administration set that contains elements both proximal and distal to the cassette, such as a drip chamber, tubing, secondary tubing connections, injection ports, and Luer connectors. The cassette offers a leak free fluid path, a passive inlet check valve with, for example, approximately 1 PSId cracking pressure, a highly flexible membrane with, for example, an approximate 1 mL stroke volume, and a passive outlet check valve with, for example, approximately 1 PSId cracking pressure. In one embodiment, the cracking pressure for each valve is at least 0.5 PSId.

The present system can be embodied in a module designed for large volume infusion pumps, wherein the module herein can be connected to a virtually unlimited source of fluid from bags or bottles or multiple syringes. This is in contrast to small volume pumps that dispense only a finite amount of contained fluid, such as a syringe pump or disposable ambulatory pump.

The disposable subsystem of the present system may be spliced into a conventional "gravity administration set," which is a typical configuration for a large volume IV pump.

The pumping subsystem of the present system is an electromechanical subassembly that may be adapted for incorporation by a pump manufacturer into a complete infusion pump product. The subassembly herein may advantageously be configured as a single off-the-shelf subassembly to replace a pump's existing mechanical architecture including doors, lever, motors, cams, springs, and drive electronics.

The present system is described herein primarily by way of reference to a flow control system for IV therapy; however, it will be recognized that the present system may be adapted for moving all manner of fluids, including enteral feeding devices and other non-medical applications.

Various system and process aspects of the invention are contemplated, including the following:

A fluid control system or process for delivery of a fluid including a controller in communication with a pressure sensor to receive sensed pressure data and in operative communication with a pneumatic drive to control incremental volume changes based on the sensed pressure data and on a predetermined fluid delivery schedule.

A fluid control system or process wherein the controller is operable to decrease a volume of gas in communication with a gas-side chamber, whereby pressure in a fluid-side chamber also decreases until a cracking pressure of an inlet valve is reached, whereupon the inlet valve opens and fluid from the fluid source enters a fluid-side chamber.

A fluid control system or process wherein the controller is operable to increase a volume of gas in communication with a gas-side chamber, whereby pressure in a fluid-side chamber also increases until a cracking pressure of an outlet valve is reached, whereupon the outlet valve opens and fluid in the fluid-side chamber exits to the fluid sink.

A fluid control system or process wherein the controller is operable to control delivery of liquid to a fluid sink by determining a volume of liquid to be delivered as the difference between a target volume of liquid to be delivered and a volume of liquid already delivered and operating the pneumatic drive in increments calculated to deliver the volume of liquid to be delivered.

A fluid control system or process wherein the controller is operable to calculate the volume of liquid to be delivered at successive time intervals and update the volume of liquid already delivered after each calculation of the volume of liquid already delivered.

A fluid control system or process wherein the controller is operable to:
  receive sensed pressure data before and after a controlled movement of a pneumatic drive,
  compare the pressure data to a known change in gas volume resulting from said controlled movement, and
  calculate a volume of gas based on the pressure data and the known change in gas volume based on an ideal gas law relationship between the sensed pressure data and the known gas volume.

A fluid control system or process wherein the controller is operable to repeat the calculation of a volume of gas based on the pressure data and the known change in gas volume over multiple times during delivery of a liquid to the fluid sink such that accumulated rate errors are eliminated from accuracy errors.

A fluid control system or process wherein the controller is operable to exert a negative pressure on a gas reservoir in fluid communication with a gas-side chamber separated from a fluid-side chamber by a flexible membrane to draw liquid from the fluid source into the fluid-side chamber through a one-way inlet valve until the fluid-side chamber fills with fluid; exert a positive pressure on the gas reservoir in fluid communication with the gas-side chamber to deliver liquid in the fluid-side chamber to the liquid sink through a one-way outlet valve; monitor pressure in the gas reservoir during the steps of exerting the negative pressure and exerting the positive pressure; and determine volumes of fluid in the fluid-side chamber from incremental changes in volume of the gas reservoir and the gas-side chamber and any connecting dead space by an ideal gas law relationship, wherein $P_1V_1=P_2V_2$, wherein $P_1$ and $P_2$ are pressures measured at two times before and after volume changes and $V_1$ and $V_2$ are volumes at the two times.

A fluid control system or process wherein the controller is operable to determine a pressure trend indicative of a hydrostatic pressure or an impedance or a resistance in the fluid flow path from the fluid source.

A fluid control system or process wherein the hydrostatic pressure or the impedance or the resistance in the fluid source is indicative of at least one of an occlusion in a line on the fluid flow path, an amount of liquid remaining in the fluid source, a viscous liquid at the fluid source, and a syringe.

A fluid control system or process wherein the controller is operable to determine a pressure trend indicative of a hydrostatic pressure or an impedance or a resistance in the fluid flow path to the fluid sink.

A fluid control system or process wherein the hydrostatic pressure of the impedance or the resistance in the fluid flow path to the fluid sink is indicative of at least one of an occlusion in a line on the fluid flow path and a disconnected connection to the fluid sink.

A fluid control system or process wherein the controller is operable to determine a pressure trend indicative of air in the fluid flow path.

A fluid control system or process wherein the controller is operable to determine a pressure trend indicative of a cracking pressure of an inlet valve or an outlet valve that is higher or lower than normal.

A fluid control system or process wherein the controller is operable to determine a pressure trend indicative of a stiction and release due to a syringe.

A fluid control system or process wherein the controller is operable to enter various states to perform a pumping cycle, the states including an unlock state in which the system is ready to start a pumping cycle.

A fluid control system or process wherein the controller is operable to enter various states to perform a pumping cycle, the states including moving a reciprocating element of a pneumatic drive to a fully refracted position of a pumping stroke.

A fluid control system or process wherein the controller is operable to enter various states to perform a pumping cycle, the states including moving a reciprocating element of a pneumatic drive to a fully advanced position of a pumping stroke.

A fluid control system or process wherein the controller is operable to enter various states to perform a pumping cycle, the states including retracting a reciprocating element of a pneumatic drive until a cracking pressure of an inlet is reached.

A fluid control system or process wherein the controller is operable to enter various states to perform a pumping cycle, the states including retracting a reciprocating element of a pneumatic drive when the inlet valve is open and liquid fills a fluid-side chamber.

A fluid control system or process wherein the controller is operable to enter various states to perform a pumping cycle, the states including advancing a reciprocating element of a pneumatic drive until a cracking pressure of an outlet valve is reached.

A fluid control system or process wherein the controller is operable to enter various states to perform a pumping cycle, the states including advancing a reciprocating element of a pneumatic drive when the outlet valve is open and liquid is delivered from the fluid-side chamber.

A fluid control system or process wherein the controller is operable to drive a pneumatic drive in controlled steps, each step providing a known volume displacement of gas volume.

A fluid control system or process wherein the controller is operable to drive a pneumatic drive in controlled steps to deliver fluid through a one-way outlet valve, wherein with each step, pressure driving the fluid first increases and then decreases as liquid leaks through the outlet valve.

A fluid control system or process wherein the controller is operable to drive a pneumatic drive in controlled steps to deliver fluid through a one-way outlet valve, and to calculate a time between steps to achieve a desired rate of infusion.

A fluid control system or process wherein the controller is operable to drive a pneumatic drive in controlled steps to deliver fluid through a one-way outlet valve, and to monitor a pressure decay after each increase in driving pressure, and to calculate a pressure value derived from the pressure decay.

A fluid control system or process wherein the controller is operable to reduce a volume of the gas reservoir by an amount that exerts a positive pressure on the gas reservoir in fluid communication with the gas-side chamber such that the positive pressure is inadequate to deliver liquid in the fluid-side change to the liquid sink and to monitor pressure in the gas reservoir during the steps of exerting the positive pressure.

A fluid control system or process wherein the controller is operable to determine volumes of fluid in the fluid-side chamber from incremental changes in volume of the gas reservoir and the gas-side chamber and any connecting dead space by an ideal gas law relationship, wherein $P_1V_1=P_2V_2$, wherein $P_1$ and $P_2$ are pressures measured at two times before and after volume changes and $V_1$ and $V_2$ are volumes at the two times; to determine a pressure trend from the step of monitoring the pressure over several time steps, and to monitor the pressure trend, the volume changes, or both for an indication of air in the fluid-side chamber.

A fluid control system or process wherein the controller is operable to determine an indication of air from a decrease in pressure during a step of filling a fluid-side chamber.

A fluid control system or process wherein the controller is operable to determine an indication of air from an increase in pressure during a step of delivering liquid that is below a normal pressure increase during the delivering step.

A fluid control system or process wherein the controller is operable to provide a comparison of a gas volume when a fluid-side chamber is fully filled with liquid to a subsequent determination of a gas volume when the fluid-side chamber contains air to determine a presence of air in the fluid-side chamber.

An infusion pumping system or process comprising a fluid flow control system including a controller, and a host controller in communication with the controller of the fluid flow control system, the host controller operable to receive instructions for determining a course of an infusion, the instructions including one of a rate of infusion or a volume of liquid to be delivered over a determined time interval, the instructions further including a start time.

An infusion pumping system including a user interface and a power supply.

An infusion pumping system including a chassis, and wherein at least a portion of a fluid flow path of the fluid flow control system, including an inlet valve and an outlet valve, and a chamber are supportable on the chassis.

It will be appreciated that the various features of the embodiments described herein can be combined in a variety of ways.

The present invention has been described with reference to the preferred embodiments. It is to be understood that the invention is not limited to the exact details of construction, operation, exact materials or embodiments shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. A process for determining presence of air in an infusion of fluid from a fluid source to a liquid sink, comprising:
    a) exerting a negative pressure on a gas reservoir in fluid communication with a gas-side chamber separated from a fluid-side chamber by a flexible membrane to draw liquid from the fluid source into the fluid-side chamber through a one-way inlet valve until the fluid-side chamber fills with fluid;
    b) reducing a volume of the gas reservoir by an amount that exerts a positive pressure on the gas reservoir in fluid communication with the gas-side chamber such that said positive pressure is inadequate to deliver liquid in the fluid-side chamber to the liquid sink through a one-way outlet valve, wherein the inlet valve and the outlet valve each comprise a passive one-way check valve having a predetermined cracking pressure, and are each configured to open only when a pressure differential between upstream fluid and downstream fluid reaches the predetermined cracking pressure;
    c) monitoring pressure in the gas reservoir during the step of exerting the positive pressure; and
    d) determining volumes of fluid in the fluid-side chamber from incremental changes in volume of the gas reservoir and the gas-side chamber and any connecting dead space by an ideal gas law relationship, wherein $P_1 V_1 = P_2 V_2$, wherein $P_1$ and $P_2$ are pressures measured at two times before and after volume changes and $V_1$ and $V_2$ are volumes at the two times;
    e) determining a pressure trend from the step of monitoring the pressure over several time steps,
    f) monitoring the pressure trend, the volume changes, or both for an indication of air in the fluid-side chamber.

2. The process of claim 1, wherein the indication of air comprises a decrease in pressure during the step of filling the fluid-side chamber.

3. The process of claim 1, wherein the indication of air comprises an increase in pressure during the step of delivering liquid that is below a normal pressure increase during the step of delivering liquid.

4. The process of claim 1, wherein the indication of air comprises a comparison of a determination of gas volume when the fluid-side chamber is fully filled with liquid to a subsequent determination of gas volume when the fluid-side chamber contains air.

5. A fluid control system for delivery of a fluid, comprising:
    a fluid flow path comprising an inlet valve configured for fluid communication with a fluid source and an outlet valve configured for fluid communication with a fluid sink;
    a chamber comprising a fluid-side chamber and a gas-side chamber, the fluid-side chamber and the gas-side chamber separated by a flexible membrane, the membrane configured so that there is substantially no pressure differential between the fluid-side chamber and the gas-side chamber across the membrane;
    the fluid-side chamber disposed on the fluid flow path downstream of the inlet valve and upstream of the outlet valve such that pressure changes in the fluid-side chamber are communicated to the inlet valve and the outlet valve;
    a pneumatically coupled drive in communication with the gas-side chamber configured to provide known incremental positive or negative volume changes that cause positive or negative pressure changes in the gas-side chamber, and wherein said pressure changes in the gas-side chamber are communicated to the fluid-side chamber via the flexible membrane, wherein the inlet valve and the outlet valve each comprise a passive one-way check valve having a predetermined cracking pressure, and are each configured to open only when a pressure differential between upstream fluid and downstream fluid reaches the predetermined cracking pressure; and
    an air elimination mechanism comprising a hydrophobic filter comprising a first side disposed in communication with the fluid-side chamber, and a second side disposed in communication with a one-way air elimination check valve, the hydrophobic filter blocking flow of liquid therethrough and allowing passage of air therethrough.

6. The system of claim 5, wherein the one-way air elimination check valve comprises a cracking pressure sufficient to allow air to pass therethrough.

7. The system of claim 5, wherein the one-way air elimination check valve comprises a cracking pressure sufficient to prevent fluid from an ambient environment to enter the system.

8. The system of claim 5, further comprising:
    a pressure sensor disposed to sense pressure in the gas-side chamber; and
    a controller in communication with the pressure sensor to receive sensed pressure data in response to a known gas volume change and to compare a pressure change sensed when a volume change is effected to the fluid-side chamber filled with liquid without air to a pressure change sensed when a volume change is effected to the fluid-side chamber filled with liquid and air, whereby a quantity of air in the fluid-side chamber is determined.

9. The system of claim 5, wherein air that has been captured and stored between the hydrophobic filter and the one-way air elimination check valve under pressure equal to the cracking pressure of the one way valve air elimination check then passes back into the fluid-side chamber when subject to a negative pressure differential, thereby to clear the hydrophobic filter of liquid.

10. The system of claim 5, wherein the filter is disposed on a wall of the fluid-side chamber and the one way air elimination check valve opens to ambient.

11. The system of claim 5, wherein the filter is disposed on the flexible membrane and the one way air elimination check valve opens to the gas-side chamber.

* * * * *